(12) United States Patent
Stead et al.

(10) Patent No.: US 7,422,873 B2
(45) Date of Patent: Sep. 9, 2008

(54) MUTANT CAROTENOID KETOLASE

(75) Inventors: Kristen Janet Stead, Wilmington, DE (US); Henry Yao, Boothwyn, PA (US); Rick W. Ye, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 404 days.

(21) Appl. No.: 11/395,644

(22) Filed: Mar. 31, 2006

(65) Prior Publication Data
US 2007/0231854 A1 Oct. 4, 2007

(51) Int. Cl.
C12P 23/00 (2006.01)
C12N 9/02 (2006.01)
C12N 1/20 (2006.01)
C12N 1/00 (2006.01)
C07H 21/04 (2006.01)

(52) U.S. Cl. .................. 435/67; 435/189; 435/320.1; 435/252.3; 435/254.1; 435/254.2; 435/254.3; 435/254.11; 435/254.6; 435/254.21; 435/254.22; 435/254.23; 435/252.31; 435/252.32; 435/252.33; 435/252.34; 435/252.35; 435/252.2; 435/257.2; 435/419; 536/23.2; 536/23.4; 536/23.7

(58) Field of Classification Search .................. 435/67, 435/189, 320.1, 252.3, 254.1, 254.2, 254.3; 536/23.2, 23.4, 23.7
See application file for complete search history.

(56) References Cited

U.S. PATENT DOCUMENTS

| 6,150,130 | A | 11/2000 | Misawa et al. | |
|---|---|---|---|---|
| 6,291,204 | B1 * | 9/2001 | Pasamontes et al. | 435/67 |
| 7,074,604 | B1 * | 7/2006 | Tang et al. | 435/189 |
| 2003/0087337 | A1 | 5/2003 | Giraud et al. | |
| 2005/0019852 | A1 | 1/2005 | Cheng et al. | |
| 2005/0214896 | A1 | 9/2005 | Cheng et al. | |

FOREIGN PATENT DOCUMENTS

| WO | WO 02/079395 A2 | 10/2002 |
|---|---|---|
| WO | WO 2005/118812 A1 | 12/2005 |
| WO | WO 2005/121352 A2 | 12/2005 |

OTHER PUBLICATIONS

CNCBI printout, Conserved domains of cd03513: CRTW_beta-carotene-ketolase, created Feb. 17, 2006.*
Ye R. et al, Mutational and Functional Anlysis of the Beta-Crotene Ketolase Involved in the Production of Canthaxantin and Astaxanthin, Appl. Environ. Microbiol. 2006, 72, 5829-5837.*
NCBI printout; GenBank Accession No. BAE47465, Nov. 1, 2005.*
U.S. Appl. No. 11/015,433, filed Dec. 17, 2004, Qiong Cheng et al.
P. Bhosale. et. al., Microbial Xanthophylls, PPL. Microbiol. Biotechnol., 2005, vol. 68:445-455.
Nelis et. al., Carotenoids From Micro-Organisms, Appl. Bacteriol., 1991, vol. 70:181-191.
N. Misawa et. al., Elucidation of the *Erwinia uredovora* Carotenoid Biosynthetic Pathway by Functional Analysis of Gene Products Expressed in *Escherichia coli*, J. Bacteriol., 1990, vol. 172:6704-6712.
N. Misawa et. al., Structure and Functional of a Marine Bacterial Carotenoid Biosynthesis Gene Cluster and Astaxanthin Biosynthetic Pathway Proposed at the Gene Level, J. Bacteriol., 1995, vol. 177:6575-6584.
Misawa et. al., Canthaxanthin Biosynthesis by the Conversion of Methylene to Keto Groups in a Hydrocarbon B-Carotene by a Single Gene, Biochem. Biophys. Res. Comm., 1995, vol. 209:867-876.
Hannibal; et. al., Isolation and Characterization of Canthaxanthin Biosynthesis Genes From the Photosynthetic Bacterium *Bradyrhizobium* so. Strain ORS278, J. Bacteriol., 2000, vol. 182:3850-3853.
Nishida et. al., Elucidation of a Carotenoid Biosynthesis Gene Cluster Encoding a Novel Enzyme, 2,2'-B-Hydroxylase, From *Brevundimonas* sp. Strain SD212 and Combinatorial Biosynthesis of New or Rare Xanthophylls, Appl. Env. Microbiol., 2005, vol. 71:4286-4296.
National Center for Biotechnology Information General Identifier No. 5912292, Sep. 15, 1999, M. Harker et. al., Carotenoid Biosynthesis Genes in the Bacterium *Paracoccus marcusii*.
P. Fraser et. al., In Vitro Characterization of Astaxanthin Biosynthesis Enzymes, J. Biol. Chem., 1997, vol. 272:6128-6135.
P. Fraser et. al., Enzymic Confirmation of Reactions Involved in Routes to Astaxanthin Formation, Elucidated Using a Direct Substrate in Vitro Assay, Eur. J. Biochem., 1998, vol. 252:229-236.
Rick W. Ye et al., Mutational and Functional Analysis of the B-Carotene Ketolase Involved in the Production of Canthaxantin and Astaxanthin, Applied and Environmental Microbiology, 2006, vol. 72:5829-5837.
International Search Report Dated Sep. 6, 2007, International Application No. PCT/US2007/006939, International Filing Date: Mar. 20, 2007.

* cited by examiner

*Primary Examiner*—Rebecca E. Prouty
*Assistant Examiner*—Malgorzata A. Walicka

(57) ABSTRACT

CrtW carotenoid ketolases are provided useful for the production of astaxanthin. The ketolases genes of the present invention exhibit improved ketolase activity when converting cyclic hydroxylated carotenoid intermediates into astaxanthin. Recombinant expression of the present carotenoid ketolases in host cell producing cyclic hydroxylated carotenoid intermediates enabled increased production of astaxanthin.

11 Claims, 1 Drawing Sheet

MUTANT CAROTENOID KETOLASE

FIELD OF THE INVENTION

Figure 1:
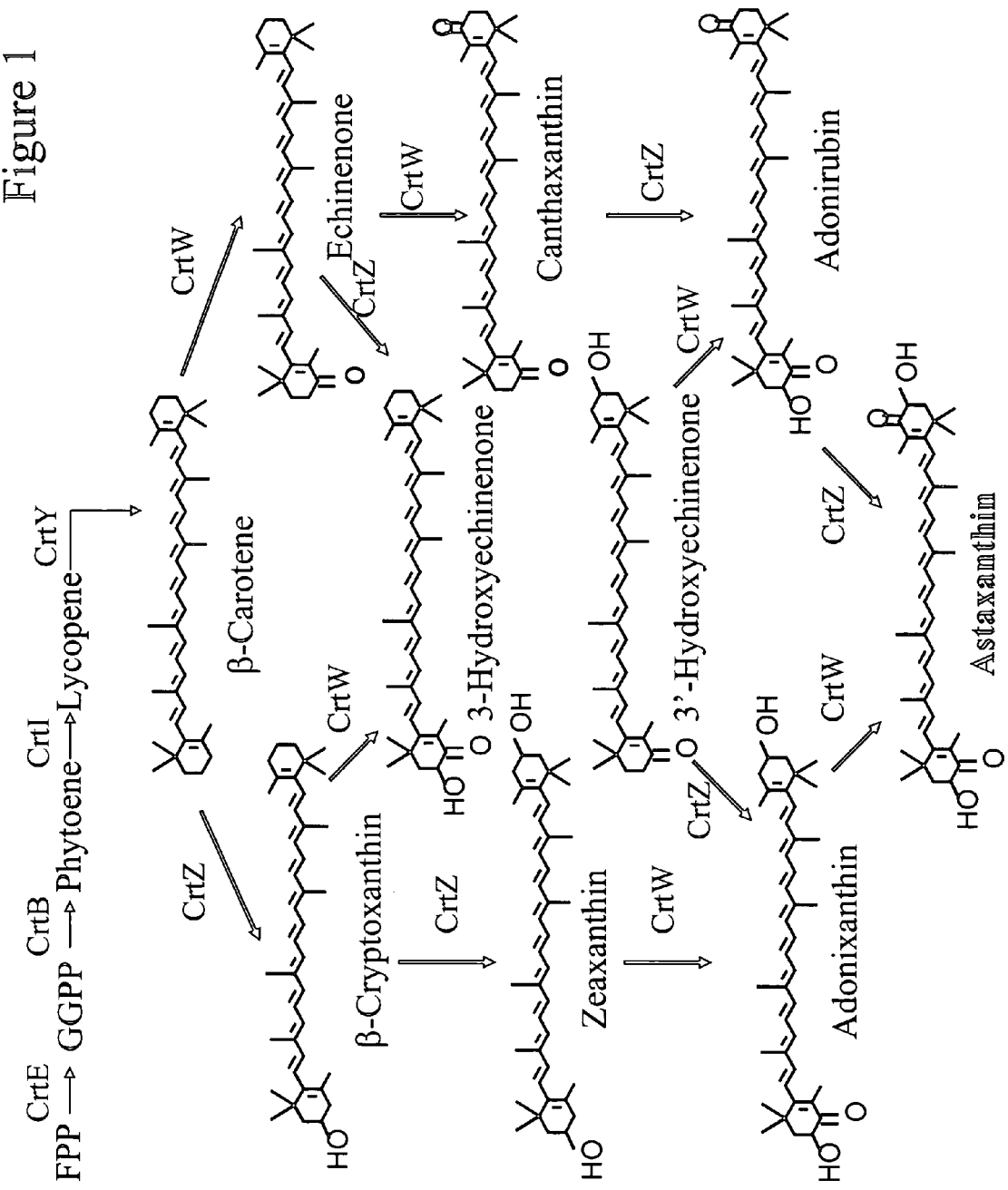

This invention is in the field of biosynthetic pathway engineering and molecular biology. More specifically, this invention pertains to nucleic acid fragments encoding polypeptides having improved carotenoid ketolase activity for the production of astaxanthin.

BACKGROUND OF THE INVENTION

Carotenoids are pigments that are ubiquitous throughout nature and synthesized by all photosynthetic organisms, and in some heterotrophic growing bacteria and fungi. Carotenoids provide color for flowers, vegetables, insects, fish and birds. Colors of carotenoid range from yellow to red with variations of brown and purple. As precursors of vitamin A, carotenoids are fundamental components in our diet and they play additional important role in human health. Because animals are unable to synthesize carotenoid de novo, they must obtain them by dietary means. Industrial uses of carotenoids include pharmaceuticals, food supplements, animal feed additives, and colorants in cosmetics, to mention a few.

Pigmentation of crustaceans, shellfish and fish (i.e., salmonids such as trout, salmon, and char) is due to the accumulation of carotenoids that are acquired through their diet. Astaxanthin is the major feed colorant used in aquaculture industry. Although chemically synthesized astaxanthin still dominates the market, biological sources of astaxanthin have been explored (Bhosale, P. and Bernstein, P. S., *Appl Microbiol Biotechnol.*, 68: 445-455 (2005) and Nelis and Leenheer, *Appl. Bacteriol.*, 70:181-191 (1991)). Both red yeast *Phaffia rhodozyma* and fresh water alga *Haematococcus pluvialis* have been used to produce natural form of the antioxidant or pigment for various applications.

Biosynthesis of astaxanthin in microorganisms requires the β-carotene biosynthetic gene cluster crtEYIB (Misawa, N., et al., *J. Bacteriol.* 172(12):6704-12 (1990)) and two β-carotenoid (β-ionone ring) modification genes crtW and crtZ (Misawa, N., et al., *J. Bacteriol.* 177(22):6575-84 (1995)). The gene cluster crtEYIB is involved in biosynthesis of β-carotene from farnesyl pyrophosphate (FPP). Synthesis of astaxanthin requires two additional genes, crtW and crtZ, encoding polypeptides that respectively introduce keto or hydroxyl groups to the β-ionone rings (FIG. 1).

The crtW gene encodes for the CrtW-type carotenoid ketolase. Carotenoid ketolases (CrtW) are enzymes that introduce keto groups to the β-ionone ring of the cyclic carotenoids, such as β-carotene, to produce ketocarotenoids (E.C. 1.13.-.-). Examples of ketocarotenoids include astaxanthin, canthaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-keto-torulene, deoxyflexixanthin, and myxobactone.

CrtW ketolases have been reported in variety of microorganisms including *Agrobacterium aurantiacum* (also known as *Paracoccus* sp. N81106; U.S. Pat. No. 6,150,130; Misawa et al., *Biochem. Biophys. Res. Comm.*, 209(3):867-876 (1995); and Misawa et al., *J. Bacteriol.*, 177(2):6575-6584 (1995)), *Bradyrhizobium* sp. (U.S. Patent Publication No. 20030087337; Hannibal et al., *J. Bacteriol.*, 182(13):3850-3853 (2000)), *Brevundimonas aurantiacum* (de Souza et al., WO 02/079395), *Brevundimonas* sp. SD212 (WO2005/118812 A1 and Nishida et al., *Appl. Env. Microbiol.*, 71(8): 4286-4296 (2005), *Paracoccus marcusii* (Harker, M. and Hirschberg, N., (GenBank® CAB56059), *Alcaligenes* sp. (Misawa et al., 1995 (supra)), *Sphingomonas melonis* DC18 (U.S. Ser. No. 11/015,433), *Brevundimonas vesicularis* (U.S. Ser. No. 11/015,433), and *Flavobacterium* sp. (U.S. Ser. No. 11/015,433).

The crtZ gene encodes the 4,4'-hydroxylase (CrtZ-type carotenoid hydroxylase) responsible for adding hydroxyl groups to β-ionone ring. Both the CrtW ketolase and the CrtZ hydroxylase are bifunctional, introducing their respective functional groups to both ionone rings on bicyclic carotenoids (Fraser, P., et al., *J Biol. Chem.*, 272(10):6128-35 (1997) and Fraser, P. et al., *Eur J Biochem.*, 252(2):229-36 (1998)). The CrtZ hydroxylase can introduce hydroxyl groups into the 3,3' positions on the β-ionone ring regardless whether there are keto groups at the 4,4'position. Likewise, the ketolase can introduce keto group at the 4,4'position regardless of the prior hydroxylation. The reaction appears to occur at one ring at a time. As a result, there are many intermediate steps when CrtW ketolases and CrtZ hydroxylases are used to produce astaxanthin.

It has been shown that CrtW ketolases and CrtZ hydroxylases from different sources have different substrate preferences. The β-carotene ketolase gene (crtW) from *Paracoccus* sp. N81106 (formerly classified as *Agrobacterium aurantiacum*) encodes a ketolase having a strong substrate preference for carotenoid β-ionone rings that are non-hydroxylated (e.g., β-carotene) and hydroxylated intermediates are poor substrates. Expression of this gene along with the carotenoid ketolase gene (crtZ) leads to accumulation of adonixanthin and other intermediates (Misawa, N., et al., *J. Bacteriol.* 177(22):6575-84 (1995)). On the other hand, expression of the crtW gene from *Brevundimonas* sp. SD212 did not lead to the accumulation of adonixanthin (Choi et al., *Mar Biotechnol.* 7:515-22 (2005)). This result suggests that the substrate specificity of the CrtW enzymes may vary among the members of this enzyme class.

One of the factors influencing the economics of recombinant microbial production of astaxanthin is the enzymatic activity of the carotenoid ketolase towards different cyclic hydroxylated intermediates. Carotenoid ketolases having limited activity toward the various cyclic hydroxylated carotenoid intermediates in the astaxanthin biosynthesis pathway generally limits astaxanthin production Carotenoid ketolases having improved activity towards these cyclic hydroxylated intermediates will increase the percentage of astaxanthin in the final product.

The problem to be solved therefore is to provide CrtW ketolases characterized by improved ketolase activity for converting cyclic hydroxylated carotenoid intermediates into astaxanthin. Furthermore, a method to produce astaxanthin using CrtW ketolases characterized by an improvement in activity for converting cyclic hydroxylated carotenoid intermediates into astaxanthin.

SUMMARY OF THE INVENTION

Mutant CrtW ketolases are provided having an improved ability to convert cyclic hydroxylated carotenoid intermediates into astaxanthin. More specifically, mutant ketolases derived from the *Paracoccus* sp. N81106 CrtW ketolase are provided characterized by improved astaxanthin synthesis activity.

In one embodiment, the invention provides an isolated nucleic acid molecule encoding a polypeptide having carotenoid ketolase activity, said polypeptide comprising an amino acid sequence as set forth in SEQ ID NO: 2 and further comprising at least one mutation selected from the group consisting of:

a) a mutation at amino acid residue 99 changing methionine to isoleucine or valine; and
b) a mutation at amino acid residue 175 changing leucine to methionine.

Preferred mutant carotenoid ketolases of the invention are those that demonstrate at least a 2.1-fold improvement in carotenoid ketolase activity relative to the *Paracoccus* sp. N81106 CrtW ketolase for converting cyclic hydroxylated carotenoid intermediates to astaxanthin under identical reaction conditions.

In additional embodiment the invention provides genetic chimera of the sequences of the invention and recombinant host cells comprising the same.

In anther embodiment the invention provides a method for the production of astaxanthin comprising:
(a) providing a host cell that produces a cyclic hydroxylated carotenoid intermediate selected from the group consisting of β-cryptoxanthin, 3-hydroxyechinenone, 3'-hydroxyechinenone, zeaxanthin, and adonixanthin;
(b) transforming the host cell of (a) with the nucleic acid molecule of the invention operably linked to suitable regulatory sequences;
(c) growing the transformed host cell of (b) under conditions whereby astaxanthin is produced.

BRIEF DESCRIPTION OF THE FIGURE AND SEQUENCE DESCRIPTIONS

FIG. 1. Illustration of possible pathway intermediates in the synthesis of astaxanthin via ketolase and hydroxylase reactions from β-carotene.

The invention can be more fully understood from the following detailed description and the accompanying sequence descriptions, which form a part of this application.

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37C.F.R. §1.822.

A Sequence Listing is provided herewith on Compact Disk. The contents of the Compact Disk containing the Sequence Listing are hereby incorporated by reference in compliance with 37 CFR 1.52(e).

SEQ ID NO: 1 is the nucleotide sequence of the coding region for the *Paracoccus* sp. N81106 (formerly *Agrobacterium aurantiacum*) crtW ketolase.

SEQ ID NO: 2 is the amino acid sequence of the *Paracoccus* sp. N81106 CrtW ketolase.

SEQ ID NO: 3 is the nucleotide sequence of primer Psub18 Kam-R.

SEQ ID NO: 4 is the nucleotide sequence of primer psub18 Kam-F.

SEQ ID NO: 5 is the nucleotide sequence of the coding region for the *Paracoccus* sp. N81106 crtZ hydroxylase gene (GenBank® D58420).

SEQ ID NO: 6 is the amino acid sequence of the *Paracoccus* sp. N81106 CrtZ hydroxylase.

SEQ ID NO: 7 is the nucleotide sequence of primer CrtZ-F (AvrII).

SEQ ID NO: 8 is the nucleotide sequence of primer CrtZ-R (BsrGI).

SEQ ID NO: 9 is the nucleotide sequence of the crt333 gene cluster (crtWEidiYIB) as described in U.S. Ser. No. 10/997,844 and U.S. Pat. No. 6,929,928).

SEQ ID NO: 10 is the nucleotide sequence of primer CrtE-F.

SEQ ID NO: 11 is the nucleotide sequence of primer Idi-R.

SEQ ID NO: 12 is the nucleotide sequence of primer CrtY-F.

SEQ ID NO: 13 is the nucleotide sequence of primer CrtB-R.

SEQ ID NO: 14 is the nucleotide sequence of primer PSUB180F-1 (fos1).

SEQ ID NO: 15 is the nucleotide sequence of primer PSU19-R(fos1).

SEQ ID NO: 16 is the nucleotide sequence of primer CrtW334 F (EcoR1).

SEQ ID NO: 17 is the nucleotide sequence of primer CrtW334-R(SacIMfe).

SEQ ID NO: 18 is the nucleotide sequence of the coding region for ketolase mutant #1 encoding a polypeptide having a mutation at amino acid residue position 175 (relative to the amino acid sequence of the *Paracoccus* sp. N81106 CrtW ketolase control) where leucine was changed to methionine (L175M; ctg →atg).

SEQ ID NO: 19 is the deduced amino acid sequence of ketolase mutant #1 having a mutation at amino acid residue position 175 wherein leucine was changed to methionine (L175M).

SEQ ID NO: 20 is the nucleotide sequence of the coding region for ketolase mutant #2 encoding a polypeptide having a mutation at amino acid residue position 99 (relative to the amino acid sequence of the *Paracoccus* sp. N81106 CrtW ketolase control) where methionine was changed to isoleucine (M99I; atg →att).

SEQ ID NO: 21 is the deduced amino acid sequence of ketolase mutant #2 having a mutation at amino acid residue position 99 where methionine was changed to isoleucine (M99I).

SEQ ID NO: 22 is the nucleotide sequence of the coding region for ketolase mutant #3 encoding a polypeptide having a mutation at amino acid residue position 99 (relative to the amino acid sequence of the *Paracoccus* sp. N81106 CrtW ketolase control) where methionine was changed to valine (M99V; atg →gtt).

SEQ ID NO: 23 is the deduced amino acid sequence of ketolase mutant #3 having a mutation at amino acid residue position 99 wherein methionine was changed to valine (M99V).

DETAILED DESCRIPTION OF THE INVENTION

The present mutant crtW genes and their expression product, CrtW-type carotenoid ketolases, are useful for the production of astaxanthin. The present enzymes are characterized by an improvement in ketolase activity when converting cyclic hydroxylated carotenoid intermediates into astaxanthin.

The nucleic acid fragment encoding the wild-type CrtW ketolase from *Paracoccus* sp. N81106 (formerly *Agrobacterium aurantiacum*) was subjected to conditions that introduced random mutations to the wild-type enzyme. A library of mutants was created and assayed for enhanced production of astaxanthin relative to the wild-type CrtW ketolase ("control") under identical reaction conditions. Several mutants were identified having improved astaxanthin production, indicating the structural changes to the present polypeptides enhanced to ketolase activity for converting cyclic hydroxylated carotenoid intermediates, such as zeaxanthin and adonixanthin, into astaxanthin.

The genes and gene products of the present invention may be used in a variety of ways for the production of astaxanthin. The present crtW ketolase genes can be used for astaxanthin production in heterologous hosts having the ability to produce suitable substrates.

The gene and gene sequences described herein enable one to incorporate the improved production of astaxanthin directly into an industrially suitable host cell. This aspect makes any recombinant host into which these genes are incorporated a more desirable production host. The astaxanthin produced can be isolated from the production host for use in a variety of applications, including animal feed. Optionally, the recombinant host cells (whole, homogenized, or autolyzed) can be directly incorporated into animal feed (no carotenoid isolation step) due to the presence of carotenoids that are known to add desirable pigmentation and health benefits. Salmon and shrimp aquacultures are particularly useful applications for this invention as carotenoid pigmentation is critically important for the value of these organisms (F. Shahidi, J. A. Brown, Carotenoid pigments in seafood and aquaculture, *Critical Reviews in Food Science*, 38(1):1-67 (1998)). Additionally, the ketocarotenoid astaxanthin is known to be a powerful antioxidant and has been reported to boost immune functions in humans and reduce carcinogenesis (Jyonouchi et al., *Nutr. Cancer*, 23:171-183 (1995); Tanaka et al., *Cancer Res.*, 55:4059-4064 (1995)).

In this disclosure, a number of terms and abbreviations are used. The following definitions are provided:

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

As used herein the term "invention" or "present invention" is not meant to be limited to specific embodiments but rather encompasses all possible embodiments of the invention as described in the claims and the specification.

"Open reading frame" is abbreviated ORF.

"Polymerase chain reaction" is abbreviated PCR.

As used herein the terms an "isolated nucleic acid molecule" and "isolated nucleic acid fragment" will be used interchangeably and will mean a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "pDCQ333" refers to a canthaxanthin producing plasmid (U.S. Ser. No. 10/997,844; herein incorporated by reference). The plasmid was constructed by cloning a codon optimized version of the *Paracoccus* sp. N81106 crtW ketolase upstream of the crtEidiYIB carotenoid gene cluster from *Pantoea agglomerans* DC404 (U.S. Pat. No. 6,929,928; herein incorporated by reference) into broad host range vector pBHR1. The resulting canthaxanthin producing gene cluster, crtWEidiYIB, was denoted as carotenoid gene cluster "crt333" (SEQ ID NO: 9).

As used herein, the term "pBADcrtZEidiYIB" refers to a zeaxanthin producing reporter plasmid. Using the crt333 gene cluster as a template, PCR amplification and ligation independent cloning (LIC) were used to amplify the crtEidiYlB genes from carotenoid gene cluster crt333. The crtZ carotenoid hydroxylase gene from *Paracoccus* sp. N81106 was cloned immediately upstream of this cluster, forming the gene cluster crtZEidiYiB. This gene cluster was cloned in pBAD/H isA (Invitrogen, Carlsbad, Calif.), forming the zeaxanthin reporter plasmid pBADcrtZEidiYIB. Expression of the carotenoid gene cluster was operably linked to an arabinose inducible promoter.

As used herein, the term "carotenoid" refers to a compound composed of a polyene backbone condensed from the five-carbon isoprene unit. Carotenoids can be acyclic or terminated with one (monocyclic) or two (bicyclic) cyclic end groups. The term "carotenoid" may include both carotenes and xanthophylls. As used herein, a "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls".

As used herein, the terms "cyclic hydroxylated carotenoid", "cyclic hydroxylated carotenoid intermediate", and "cyclic hydroxylated intermediate" refer to C40 carotenoids derived from β-carotene having a least hydroxyl group on the β-ionone ring. Carotenoid hydroxylases (e.g., CrtZ) and carotenoid ketolases (e.g., CrtW) are enzymes that typically accept a variety of carotenoid substrates in the biosynthetic pathway from β-carotene to astaxanthin, although the activity towards each substrate varies (FIG. 1). In one embodiment, the cyclic hydroxylated intermediates in the biosynthetic pathway to astaxanthin include, but are not limited to β-cryptoxanthin, 3-hydroxyechinenone, 3'-hydroxyechinenone, zeaxanthin, and adonixanthin.

As used herein, the term "carotenoid biosynthetic pathway" refers to those genes comprising members of the "upper isoprenoid pathway" and/or the "lower carotenoid biosynthetic pathway".

As used herein, the terms "upper isoprenoid pathway" and "upper pathway" are used interchangeably and refer to enzymes involved in converting pyruvate and glyceraldehyde-3-phosphate to farnesyl pyrophosphate (FPP). Genes encoding these enzymes include, but are not limited to: the "dxs" gene (encoding 1-deoxyxylulose-5-phosphate synthase); the "dxr" gene (encoding 1-deoxyxylulose-5-phosphate reductoisomerase; also known as the ispC); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase; also known as ispF); the "lytB" gene (also known as ispH) involved in the formation of dimethylallyl diphosphate; the "gcpE" gene (also known as ispG) involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

As used herein, the terms "lower carotenoid biosynthetic pathway" and "lower pathway" will be used interchangeably and refer to those enzymes which convert FPP to a suite of carotenoids. These include those genes and gene products that are involved in the synthesis of astaxanthin. These genes and gene products comprise all of the "crt" genes including, but not limited to: crtE, crtY, crtI, crtB, crtZ, and crtW Finally, the term "lower carotenoid biosynthetic enzyme" is an inclusive term referring to any and all of the enzymes in the lower pathway including, but not limited to: CrtE, CrtY, CrtI, CrtB, CrtZ, and CrtW.

As used herein, the term "CrtE" refers to a geranylgeranyl pyrophosphate synthase enzyme encoded by the crtE gene and which converts trans-trans-farnesyl diphosphate and isopentenyl diphosphate to pyrophosphate and geranylgeranyl diphosphate.

As used herein, the term "CrtY" refers to a lycopene cyclase enzyme encoded by the crtY gene, which converts lycopene to β-carotene.

As used herein, the term "CrtI" refers to a phytoene desaturase enzyme encoded by the crtI gene. CrtI converts phytoene into lycopene via the intermediaries of phytofluene, ζ-carotene, and neurosporene by the introduction of 4 double bonds.

As used herein, the term "CrtB" refers to a phytoene synthase enzyme encoded by the crtB gene, which catalyzes the reaction from prephytoene diphosphate to phytoene.

As used herein, the term "CrtZ" refers to a β-carotene hydroxylase enzyme encoded by the crtZ gene, which catalyzes a hydroxylation reaction from β-carotene to zeaxanthin.

As used herein, the term "CrtW" refers to a β-carotene ketolase enzyme encoded by the crtW gene, which catalyzes an oxidation reaction where a keto group is introduced on the ionone ring of cyclic carotenoids. The term "carotenoid ketolase" or "ketolase" refers to the group of enzymes that can add keto groups to the ionone ring of cyclic carotenoids.

As used herein, the term "keto group" or "ketone group" will be used interchangeably and refers to a group in which a carbonyl group is bonded to two carbon atoms: $R_2C=O$ (neither R may be H).

As used herein, the term "ketocarotenoid" refers to carotenoids possessing at least one keto group on the ionone ring of a cyclic carotenoid. Examples of ketocarotenoids include, but are not limited to canthaxanthin and astaxanthin. In the present invention, mutant carotenoid ketolases are provided characterized by their ability to increase astaxanthin production in the presence of suitable substrates.

As used herein, the term "codon degeneracy" refers to the nature in the genetic code permitting variation of the nucleotide sequence without effecting the amino acid sequence of an encoded polypeptide. Accordingly, the instant invention relates to any nucleic acid fragment encoding a polypeptide having an amino acid sequence selected from the group SEQ ID NOs: 19, 21, and 23. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, the term "coding sequence" refers to a DNA sequence that codes for a specific amino acid sequence. As used herein, the term "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, ribosomal binding sites, effector binding sites, and stem-loop structures.

As used herein, the term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

As used herein, the term "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

As used herein, the term "transformation" refers to the transfer of a nucleic acid fragment into the genome of a host organism, resulting in genetically stable inheritance. As used herein, the host cell genome includes both chromosomal or extrachromosomal (i.e., a vector) genes with the host cell. Host organisms containing the transformed nucleic acid fragments are referred to as "transgenic", "recombinant" or "transformed" organisms.

As used herein, the terms "plasmid", "vector", and "cassette" refer to an extrachromosomal element often carrying genes usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The present invention provides mutant crtW genes encoding polypeptides having improved ketolase activity for converting cyclic hydroxylated carotenoid intermediates into astaxanthin. Comparisons in astaxanthin production between the recombinantly expressed mutant crtW ketolase genes and the control (wild type crtW ketolase gene from *Paracoccus* sp. N81106; SEQ ID NOs: 1-2) indicate that the present mutations have an improvement in ketolase activity when converting cyclic hydroxylated carotenoid intermediates (see FIG. 1) into astaxanthin (Table 1). The present CrtW ketolases may be used in vitro and/or in vivo for the production of ketocarotenoids from cyclic carotenoid compounds.

Mutant Carotenoid Ketolases

As used herein, the terms "mutant carotenoid ketolase", "improved carotenoid ketolase", and "mutant CrtW ketolase" refer to the present carotenoid ketolases exhibiting an improved activity for converting hydroxylated carotenoids to astaxanthin. The mutant carotenoid ketolases were created by mutating the CrtW ketolase from *Paracoccus* sp. N81106. Improvements in activity were measured relative to the control (i.e., the ketolase activity of the *Paracoccus* sp. N81106 CrtW ketolase assayed under identical reaction conditions). The present mutant carotenoid ketolases are comprised of at least one amino acid substitution relative to the CrtW ketolase from *Paracoccus* sp. N81106 (SEQ ID NO: 2). As such, each of the present mutant ketolases have the amino acid sequence of SEQ ID NO: 2 and at least one amino acid substitution selected from the list of mutations provided herein that increase astaxanthin production. In one embodiment, the present mutant carotenoid ketolases have the amino acid sequence of SEQ ID NO: 2 and at least one amino acid substitution selected from the group consisting of M99I, M99V, and L175M. In a further embodiment, the present mutant ketolase genes comprise a nucleotide acid sequence encoding a CrtW ketolase having the amino acid sequence of SEQ ID NO: 2 and at least one amino acid substitution selected from the group consisting of M99I, M99V, and L175M. In yet a further embodiment, the present mutant CrtW ketolase enzyme comprise an amino acid sequence selected from the group consisting of SEQ ID NO: 19, SEQ ID NO: 21, and SEQ ID NO: 23. In still yet a further embodiment, the nucleic acid sequence of the present mutant crtW ketolase coding region is selected from the group consisting of SEQ ID NO: 18, SEQ ID NO: 20, and SEQ ID NO: 22.

The present mutant CrtW ketolases exhibit a significant improvement in activity for converting cyclic hydroxylated carotenoid intermediates into astaxanthin. As used herein, a "significant improvement" is defined as having at least a 2.1-fold improvement in carotenoid ketolase activity when converting cyclic hydroxylated carotenoid intermediates into astaxanthin when compared to the activity of the *Paracoccus* sp. N81106 CrtW ketolase (SEQ ID NO: 2) under identical reaction conditions. The activity is measured by the percentage of astaxanthin produced relative to the total carotenoid titer. In a preferred embodiment, the present mutant CrtW ketolases exhibit an improved activity for converting zeaxanthin and/or adonixanthin to astaxanthin.

Genes Involved in Carotenoid Production

The enzymatic pathway involved in the biosynthesis of carotenoids can be conveniently viewed in two parts, the upper isoprenoid pathway providing for the conversion of pyruvate and glyceraldehyde-3-phosphate to farnesyl pyrophosphate (FPP) and the lower carotenoid biosynthetic pathway, which provides for the synthesis of phytoene and all subsequently produced carotenoids. The upper pathway is ubiquitous in many non-carotenogenic microorganisms and in these cases it will only be necessary to introduce genes that comprise the lower pathway for the biosynthesis of the desired carotenoid. The key division between the two pathways concerns the synthesis of farnesyl pyrophosphate. Where FPP is naturally present, only elements of the lower carotenoid pathway will be needed. However, it will be appreciated that for the lower pathway carotenoid genes to be effective in the production of carotenoids, it will be necessary for the host cell to have suitable levels of FPP within the cell. In another embodiment, isoprenoid biosynthesis genes may be optionally upregulated to increase the levels of FPP available for carotenoid biosynthesis. Where FPP synthesis is not provided by the host cell, it will be necessary to introduce the genes necessary for the production of FPP. Each of these pathways will be discussed below in detail.

The Upper Isoprenoid Pathway

Isoprenoid biosynthesis occurs through either of two pathways, generating the common C5 isoprene sub-unit, isopentenyl pyrophosphate (IPP). First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.*, 111:135-140 (1993); Rohmer et al., *Biochem.*, 295: 517-524 (1993); Schwender et al., Biochem., 316: 73-80 (1996); and Eisenreich et al., *Proc. Natl. Acad. Sci. USA*, 93: 6431-6436 (1996)).

Many steps in the mevalonate-independent isoprenoid pathway are known. For example, the initial steps of the alternate pathway leading to the production of IPP have been studied in *Mycobacterium tuberculosis* by Cole et al. (*Nature*, 393:537-544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4- phosphate. One of the enzymes involved in the isomerization and reduction process is D-1-deoxyxylulose-5-phosphate reductoisomerase (DXR), encoded by the gene dxr (also known as ispC). 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP. Recently, however, the ygbP gene was renamed as ispD as a part of the isp gene cluster (SwisProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. YchB phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). YgbB converts 4-diphosphocytidyl-2C-methyl-D-erythritol 2-phosphate to 2C-methyl-D-erythritol 2,4-cyclodiphosphate in a CTP-dependent manner. This gene has also been recently renamed as ispF (SwissProtein Accession #P36663).

The enzymes encoded by the gcpE (also known as ispG) and lytB (also known as ispH) genes (and perhaps others) are thought to participate in the reactions leading to formation of isopentenyl pyrophosphate (IPP) and dimethylallyl pyrophosphate (DMAPP). IPP may be isomerized to DMAPP via IPP isomerase, encoded by the idi gene. However, this enzyme is not essential for survival and may be absent in some bacteria using 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

The synthesis of FPP occurs via the isomerization of IPP to dimethylallyl pyrophosphate. This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule).

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the first step in the lower carotenoid biosynthetic pathway is considered to begin with the prenyltransferase reaction converting farnesyl pyrophosphate (FPP) to geranylgeranyl pyrophosphate (GGPP). The gene crtE, encoding GGPP synthetase, is responsible for this prenyltransferase reaction which adds IPP to FPP to produce the 20-carbon molecule GGPP. A condensation reaction of two molecules of GGPP occurs to form phytoene (PPPP), the first 40-carbon molecule of the lower carotenoid biosynthesis pathway. This enzymatic reaction is catalyzed by crtB, encoding phytoene synthase.

Lycopene is produced from phytoene through four sequential dehydrogenation reactions by the removal of eight atoms of hydrogen, catalyzed by the gene crtI (encoding phytoene desaturase). Intermediaries in this reaction are phytofluene, zeta-carotene, and neurosporene.

Lycopene cyclase (crtY) converts lycopene to β-carotene. In the present invention, an arabinose inducible reporter plasmid is used that produces zeaxanthin (pBADcrtZEidiYIB; Example 1). β-carotene is converted to zeaxanthin via a hydroxylation reaction resulting from the activity of β-carotene hydroxylase (encoded by the crtZ gene). β-cryptoxanthin is an intermediate in this reaction.

Preferred sources of the non-crtW carotenoid genes are from *Pantoea stewartii* (ATCC 8199; WO 02/079395), *Pantoea stewartii* DC413 (U.S. Ser. No. 10/810,733), *Enterobacteriaceae* DC260 (U.S. Ser. No. 10/808,979), *Pectobacterium cypripedii* DC416 (U.S. Ser. No. 10/804,677), *Brevundimonas vesicularis* DC263 (U.S. Ser. No. 11/015,433), *Sphingomonas melonis* DC18 (U.S. Ser. No. 11/015,433), and *Pantoea agglomerans* DC404 (U.S. Ser. No. 10/808,807).

Recombinant Expression—Microbial

The gene and gene product of the instant sequences may be produced in heterologous host cells, particularly in the cells of microbial hosts. Expression in recombinant microbial hosts may be useful for the expression of various pathway intermediates, for the modulation of pathways already existing in the host, or for the synthesis of new products heretofore not possible using the host.

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to bacterial, fungal or yeast species such as *Aspergillus, Trichoderma, Saccharomyces, Pichia, Candida, Phaffia, Yarrowia, Hansenula*, or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, suitable bacterial host strains include *Escherichia, Bacillus*, and *Methylomonas*.

Microbial expression systems and expression vectors containing regulatory sequences that direct high-level expression of foreign proteins are well known to those skilled in the art.

Any of these could be used to construct chimeric genes for expression of present ketolases. These chimeric genes could then be introduced into appropriate microorganisms via transformation to provide high level expression of the enzymes Accordingly, it is expected that introduction of chimeric genes encoding the instant bacterial enzymes under the control of the appropriate promoters will demonstrate increased or altered cyclic ketocarotenoid production. It is contemplated that it will be useful to express the instant genes both in natural host cells as well as heterologous host. Introduction of the present crtW genes into native host will result in altered levels of existing ketocarotenoid production. Additionally, the instant genes may also be introduced into non-native host bacteria where the existing carotenoid pathway may be manipulated.

The present CrtW ketolases have been selected for their increased activity when converting cyclic hydroxylated carotenoid intermediates to produce astaxanthin. Specific cyclic hydroxylated carotenoid intermediates may include, but are not limited to zeaxanthin, β-cryptoxanthin, adonirubin, adonixanthin, 3-hydroxyechinenone, and 3'-hydroxyechinenone (FIG. 1). In one embodiment, the present CrtW ketolases exhibit an improvement when converting zeaxanthin and/or adonixanthin to astaxanthin.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*, and promoters isolated from the nrtA, gInB, moxF, glyoxil, htpG, and hps genes useful for expression in *Methylomonas* (U.S. Ser. No. 10/689,200). Additionally, promoters such as the chloramphenicol resistance gene promoter may also be useful for expression in *Methylomonas*.

Termination control regions may also be derived from various genes native to the preferred hosts. Optionally, a termination site may be unnecessary, however, it is most preferred if included.

Knowledge of the sequence of the present gene will be useful in manipulating the carotenoid biosynthetic pathways in any organism having the ability to produce suitable substrates. Methods of manipulating genetic pathways are common and well-known in the art. Selected genes in a particularly pathway may be upregulated or down regulated by variety of methods. Additionally, competing pathways organism may be eliminated or sublimated by gene disruption and similar techniques.

Once a key genetic pathway has been identified and sequenced specific genes may be upregulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively, it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.*, 171:4617-4622 (1989), Balbas et al., *Gene*, 136: 211-213 (1993), Gueldener et al., *Nucleic Acids Res.*, 24:2519-2524 (1996), and Smith et al., *Methods Mol. Cell. Biol.*, 5:270-277 (1996)).

Industrial Production

Where commercial production of astaxanthin is desired using the present mutant crtW genes, a variety of culture methodologies may be applied. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system with the exception that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36:227, (1992).

Commercial production of astaxanthin may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, methane, and/or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1Compd.*, [Int. Symp.], 7th (1993), 415-32. Editor(s): Murrell, J. Collin; Kelly, Don P. Publisher: Intercept, Andover, U.K). Similarly, various species of *Candida* will metabolize alanine or oleic acid (Sulter et al., *Arch. Microbiol.*, 153:485-489 (1990)). Hence it is contemplated that the source of carbon utilized in the present invention may encompass a wide variety of carbon containing substrates and will only be limited by the choice of organism.

Recombinant Expression—Plants

Plants and algae are also known to produce carotenoid compounds. The nucleic acid fragments of the instant invention may be used to create transgenic plants having the ability to express the microbial protein. Preferred plant hosts will be any variety that will support a high production level of the instant proteins. Suitable green plants will include, but are not limited to soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*, L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, but not limited to commercially significant hosts such as *Spirulina, Haemotacoccus*, and *Dunaliela*. Production of the carotenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences or the present invention should be capable of promoting expression of the present gene product. High-level plant promoters that may be used in this invention include the promoter of the small subunit (ss) of the ribulose-1,5-bisphosphate carboxylase from example from soybean (Berry-Lowe et al., *J. Molecular and App. Gen.*, 1:483-498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, NY (1983), pages 29-38; Coruzzi, G. et al., *J. Biol. Chem.*, 258:1399 (1983), and Dunsmuir, P. et al., *J. Mol. Appl. Gen.*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus that multiple events must be screened in order to obtain lines displaying the desired expression level and pattern. Such screening may be accomplished by Southern analysis of DNA blots (Southern, *J. Mol.*

Biol., 98:503 (1975)). Northern analysis of mRNA expression (Kroczek, *J. Chromatogr. Biomed. Appl.*, 618 (1-2):133-145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell*, 56:247-253 (1989)), signal sequences or sequences encoding endoplasmic reticulum localization (Chrispeels, J. J., *Ann. Rev. Plant Phys. Plant Mol. Biol.*, 42:21-53 (1991)), or nuclear localization signals (Raikhel, N., *Plant Phys.*, 100:1627-1632 (1992)) added and/or with targeting sequences that are already present removed. While the references cited give examples of each of these, the list is not exhaustive and more targeting signals of utility may be discovered in the future that are useful in the invention.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories/BD Diagnostics (Sparks, Md.), Promega (Madison, Wis.), New England Biolabs (Beverly, Mass.), Invitrogen (GIBCO/BRL) Life Technologies (Carlsbad, Calif.), or Sigma Chemical Company (St. Louis, Mo.) unless otherwise specified.

The meaning of abbreviations is as follows: "h" means hour(s), "min" means minute(s), "seq" means second(s), "d" means day(s), "mL" means milliliters, "µL" mean microliters, "L" means liters, "g" means grams, "mg" means milligrams, "µg" means micrograms, and "ppm" means parts per million.

Example 1

Construction of the Zeaxanthin Expression System

Biosynthesis of zeaxanthin in *E. coli* requires the expression of the crtZ gene and crtEYIB gene cluster. The crtZ gene encodes a carotenoid hydroxylase, while the gene cluster is involved in biosynthesis of β-carotene. To combine these genes into a single cluster, a ligation independent cloning (LIC) method based on α-phosphorothioate (PTO) nucleotide modified primers was used (da Costa, L. and Tanuri, A., *J. Virol. Meth.*, 72:117-121 (1998); Zhou, M. and Hatahet, Z., *Nucleic Acids Res.*, 23(6):1089-1090 (1995); and U.S. Ser. No. 10/972,185; herein incorporated by reference). In this procedure, multiple α-thiol linkages are introduced in the primers and used to stop the digestion of the T7 exonuclease at a specific site from 5' end of the DNA strand, thus generating complementary region for annealing. In the present examples, the α-thiol linkages (PTO modifications) are represented by an "X" within the nucleic acid sequence listed. The α-thiol linkages indicated in the sequences provided in the following examples have been removed for preparation of the sequence listing. Since these complementary overhangs used are long, ligation is not necessary before transformation. The annealed structure can be directly transformed into competent *E. coli* cells. For assembling zeaxanthin gene cluster, a 14 nucleotide complementary region was used. The order of annealing is vector-crtZ-crtEidi-crtYIB-vector.

The vector for cloning was based on pSU18 (Martinez et al., *Gene*, 68:159-162 (1988)) and it was amplified with the primer set PSub18 Kam-R (5-tgttacaaccaattaXaXcXcXaattc-3'; SEQ ID NO: 3) and PSub18 Kam-F (5'-cgcgctagaattccaX-cXcXaXtcatacactaaatcagtaag-3'; SEQ ID NO: 4). The crtZ gene (SEQ ID NOs: 5-6; GenBank® D58420) from *Paracoccus* sp. N81106 (formerly classified as *Agrobacterium aurantiacum*) was amplified with primer set CrtZ-F (AvrII) (5'-aattggttgtaacagXaXaXtXtccctaggtctagaaaggaggaataaacc atgacca-3'; SEQ ID NO: 7) and CrtZ-R (BsrGI) (5'-ctcgacta-gaattgtXgXtXaXcattaggtgcgttcttgggcttcggca-3'; SEQ ID NO: 8). The crtE and idi genes from crt333 gene cluster (SEQ ID NO: 9; U.S. Ser. No. 10/997,844 and U.S. Pat. No. 9,929,928) were amplified with CrtE-F (5'-caattctagtcgagaXcXgX-cXcgggtaccaaccatgacaagaccctttgaaacacatcc-3'; SEQ ID NO: 10) and Idi-R (5'-atcagatcccattttXtXtXcXatac-cgctccccggtataa-3'; SEQ ID NO: 11) primers, while the crtYIB gene cluster from the crt333 gene cluster (SEQ ID NO: 9) was amplified with primers CrtY-F (5'-aaatgggatct-gattXcXtXgXgtcggcg-3'; SEQ ID NO: 12) and CrtB-R (5'-ggaattctagcgcggXgXcXgXctgccag-3'; SEQ ID NO: 13). After PCR amplification, the samples were treated with DpnI and DNA fragments were purified from agarose gel. In the standard LIC reaction, 30 ng of each DNA fragment was mixed in the same tube and treated with 10 units of T7 exonuclease (New England Biolabs; Beverly, Mass.) for 5 min at 30° C. in the NT buffer. NT buffer is a combination of the two buffer systems, NEB buffer 4 and TM buffer. The TM buffer (10×) consisted of 500 mM of Tris-HCl (pH 8.0) and 100 mM $MgCl_2$. The reaction mixture was placed in a PCR tube and reaction was carried out in a thermocycler with the following conditions: 5 min at 30° C. for enzyme digestion, 3 min at 72° C. for denaturing the single stranded ends, and then followed by one cycle of annealing (65° C., 1 min; 60° C., 1 min; 55° C., 1 min; 50° C., 1 min; 45° C., 1 min; 40° C., 1 min; 37° C., 10 min; 22° C. for 10 min). An aliquot (2 µL of the 20-µL reaction mixture) was used for transformation with chemical competent cells (*E. coli* Top 10; Invitrogen, Carlsbad, Calif.). The transformants were then grown on LB media with kanamycin (Km) (50 µg/mL).

After overnight growth, yellow colonies were picked and plasmid DNA was isolated. Restriction enzyme digestion and PCR amplification for the presence of the crtZ gene was used to confirm the proper assembling of the gene cluster. After assembling, the zeaxanthin gene cluster was isolated as an EcoRI fragment and subcloned into the pBAD/HisA (Invitrogen) vector such that the zeaxanthin production is subjected to L-arabinose induction. The resulting construct was designated as pBADcrtZEidiYIB (zeaxanthin reporter construct).

Example 2

Construction of an Expression System for Low-Level Expression of crtW

The strategy to design a screening system to identify CrtW variants having higher activity for cyclic hydroxylated carotenoid substrates is based on their colors. When the expression level of the crtW gene on a separate plasmid is low, *E. coli* cells hosting the zeaxanthin construct pBAD-crtZEidiYIB will accumulate large amount of zeaxanthin and adonixanthin. Since both products are yellow, the colonies appear yellowish. If the activity of the CrtW enzyme has been improved after mutagenesis, more of the zeaxanthin and adonixanthin will be converted to astaxanthin in the cell. Since the astaxanthin has an orange color, the colonies will appear orange.

To express a low level of the crtW gene, the low copy number plasmid pSU18 was used (Martinez et al., *Gene*, 68:159-162 (1998)). The pSU18 vector was amplified with primer sets PSUB180F-1 (fos1) (5'-taacgatgcaaaacgcatcctgc-caXcXcXaXtcatacactaaatcagtaag-3'; SEQ ID NO: 14) and PSU18-R(fos1) (5'-tttcagcgacaactcctgcattggcXaX-tXaXcgagccggaagcataaagtg-3'; SEQ ID NO: 15). The crtW-gene (SEQ ID NO: 1) from *Paracoccus* sp. N81106 was amplified with CrtW334 F (EcoR1) (5'-tcatccggaaftcactag-taaggagg-3'; SEQ ID NO: 16) and CrtW334-R(SacIMfe) (5'-atcaattggagctcgtttattcctcctttctagatcacg-3'; SEQ ID NO: 17).

After amplification, these two fragments were gel purified. The insert was phosphorylated before the blunt end ligation reaction. After ligation, the mixture was transformed into electrocompetent *E. coli* Top 10 cells containing pBAD-crtZEidiYIB. There are two possible orientations for crtW gene after ligation. The orientation that produced less intense color and stayed yellowish after overnight growth was used in the screen system. This construct was designated as pSU18crtW.

Example 3

Mutagenesis of the crtW gene and Screening of Positive Clones

The in vitro mutagenesis of crtW gene was carried out with the error-prone PCR kit (GeneMorph® II Random Mutagenesis kit, Stratagene, La Jolla, Calif.). The first library was constructed with the template DNA generated by amplifying the crtW gene (SEQ ID NO: 1) with primer set CrtW334 F (EcoR1) (SEQ ID NO: 19) and CrtW334-R(SacIMfe) (SEQ ID NO: 20) with a high fidelity enzyme Pfx (Invitrogen). The amount of template used for error-prone PCR was 100 ng and 25 rounds of amplification was carried out in order to achieve 0-4 mutations per kilobase (kb) of sequence. The second library used the error-prone PCR product from the first library as template. The PCR products were gel purified and digested with EcoRI and SacI. The cloning vector was prepared by digesting the pSU18crtW construct with EcoR1 and SacI. After ligation, the reaction mixture was transformed into *E. coli* TOP10 cells harboring the pBADcrtZEidiYIB plasmid via electroporation. The *E. coli* culture was spread on large LB plates (9×9-inch Low profile square bioassay dishes, Corning Life Sciences, Acton, Mass.). The LB was supplemented with 100 µg/L ampicillin, 12.3 µg/L Cm, and 0.002% L-arabinose. Spreading of the transformation sample was aided with glass beads. The plates were incubated at 37° C. overnight, followed by another overnight at room temperature. Those colonies with a bright orange color were chosen for further analysis by sequencing.

Sequencing results revealed that six of the positive clones had a change in the amino acid residue 175. The leucine in this position was changed to a methionine (SEQ ID NO: 18-19 L175M; ctg→atg). In addition, there were three positive clones had a change in amino acid residue 99. The methionine in this position was changed to either an isoleucine (SEQ ID NO: 20-21; M99I; atg→aft) or a valine (SEQ ID NO:22-23; M99V; atg→gtt).

Example 4

HPLC Analysis of the L175M. M99I, and M99L Mutants

In order to investigate the carotenoid intermediate profiles, strains containing the wild type as well as the mutated crtW genes were grown in 10-mL of LB solution supplemented with antibiotics ampicillin (50 µg/mL) and Cm (12.5 µg/mL) and 0.002% L-arabinose. The ampicillin was used to maintain the reporter plasmid pBADcrtZEidiYIB and Cm was used to maintain the pSU18 vector with the crtW gene. The overnight culture with antibiotics, but without L-arabinose, was used to inoculate the 10-mL LB medium. After 8 or 16 hours of growth, the 10-mL samples were collected in a Corning 50-mL disposable polypropylene tube and centrifuged at 8000 rpm for 10 minutes. The cell pellet was then either frozen at −80° C. or processed following centrifugation.

Sample Preparation

Cell pellets were disrupted prior to analysis using the following protocol. Frozen cell pellets were thawed completely prior to using the following protocol.

1. Approximately 0.1 mm glass beads were added (~0.5 mL) to the cell pellet.
2. Ethanol (2 mL) was then added and the resulting material was vortexed until the cell pellet was in solution.
3. Dichloromethane (3 mL) was added to the tube.

4. The capped tube was vortexed for about 2 minutes while occasionally cracking the lid open for gas to escape and relieve pressure build-up.
5. The sample was then centrifuged at 8000 rpm for 10 minutes.
6. The supernatant was transferred to a new 50-mL Corning polypropylene centrifuge tube.
7. The supernatant was dried down using nitrogen.
8. The dried sample was dissolved in 2-mL total volume chloroform/hexane (4.5% chloroform) mixture. Approximately 90 μL of chloroform was added to the sample followed by gentle mixing until all of the carotenoid was dissolved. Approximately 1910 μL of HPLC-grade hexane was then added.
9. The sample was then filtered through a 0.2 μm Gelman Teflon syringe filter (Gellman/Pall Life Science, Ann Arbor, Mich.) and perform HPLC analysis on filtrate.

HPLC Analysis

The sample filtrate containing all-E and various Z-astaxanthin isomers and other carotenoids was analyzed using Beckman System Gold® HPLC (Beckman Coulter, Fullerton, Calif.) equipped with a model 125 ternary pump system, model 168 diode array detector, and model 508 autosampler. A 20 μL of concentrated cell extract was injected onto a 250×4.6 mm Brownlee, Spheri-5 Silica-5 μm normal phase HPLC column (Perkin Elmer, Part No. 01720023) protected by a 30×4.6 mm Brownlee Spheri-5 silica 5 um guard column (Perkin Elmer, Part No. 07110031). Retention time and spectral comparison confirmed peak identity with all-E astaxanthin standards as well as other carotenoid standards (canthaxanthin, adonirubin, adonixanthin, zeaxanthin, lycopene, echinenone, β-carotene) in the wavelength range from 220 to 600 nm. The retention time and spectral profiles of astaxanthin were an exact match to those obtained from the pure component astaxanthin standards. Astaxanthin was quantified by comparison of area counts with a previously determined calibration curve as described below. A wavelength of 470 nm, corresponding to the maximum absorbance wavelength of astaxanthin in 4.5% chloroform/94.5% n-hexane, was used for quantification. A mobile phase consisting of 14% acetone and 86% n-hexane was used for normal phase separation of all-E and various Z-astaxanthin isomers. The separation of astaxanthin was accomplished isocratically at a flow rate of 1.5 mL/min for 20 minutes. A parallel astaxanthin separation by a dual pump system (Pump A at 14% acetone; Pump B at 86% n-hexane) using the same Beckman HPLC pump Model 125, yielded identical results.

Astaxanthin calibration curves were prepared from stock solutions by dissolving 1 mg of astaxanthin (CaroteNature, Switzerland) in 10 mL of 4.5% chloroform/94.5% hexane solution. Appropriate dilutions of this stock solution were made to span the astaxanthin concentrations encountered in the extracts. Calibration curves constructed in this manner were linear over the concentration range examined.

Results of the HPLC analysis of all four mutants show an increase in the production of astaxanthin (Table 1). The amount of astaxanthin produced in strains carrying M99I or M99V were similar (32.1% and 33.0%, respectively) and was higher than the wild type (control; 15.1%). The amount of astaxanthin produced with the L175M (50.8%) was higher than that for M99L or M99I.

TABLE 1

HPLC analysis of various CrtW mutants in a reporter strain comprising a zeaxanthin biosynthetic gene cluster. A percentage of various products are reported.

| Mutant # | Mutation | Zeaxanthin (%) | Adonxixanthin (%)) | Astaxanthin (%) | Fold Increase |
|---|---|---|---|---|---|
| Control (SEQ ID NO: 2) | — | 36.4 | 41.7 | 15.1 | — |
| 1 (SEQ ID NO: 19) | L175M ctg → atg | 5.1 | 19.9 | 50.8 | 3.4 |
| 2 (SEQ ID NO: 21) | M99I atg → att | 12.6 | 40.6 | 32.1 | 2.1 |
| 3 (SEQ ID NO: 23) | M99V atg → gtt | 12.0 | 47.1 | 33.0 | 2.2 |

What is claimed is:

1. An isolated nucleic acid molecule encoding a polypeptide having carotenoid ketolase activity, said polypeptide comprising an amino acid sequence as set forth in SEQ ID NO: 2 with one mutation selected from the group consisting of:
   a) a mutation at amino acid residue 99 changing methionine to isoleucine;
   b) a mutation at amino acid residue 99 changing methionine to valine; and
   c) a mutation at amino acid residue 175 changing leucine to methionine.

2. An isolated nucleic acid molecule of claim 1 wherein said polypeptide has at least a 2.1- fold increase in carotenoid ketolase activity relative to the *Paracoccus* sp. N81106 CrtW ketolase for converting cyclic hydroxylated carotenoid intermediates to astaxanthin under identical reaction conditions.

3. The isolated nucleic acid molecule according to claim 1 encoding a polypeptide having an amino acid sequence selected from the group consisting of SEQ ID NO: 19, SEQ ID NO: 21, and SEQ ID NO: 23.

4. The isolated nucleic acid molecule of claim 1 comprising a nucleic acid sequence selected from the group consisting of SEQ ID NO: 18, SEQ ID NO: 20, and SEQ ID NO: 22.

5. A chimeric gene comprising the isolated nucleic acid molecule of claim 1 operably linked to suitable regulatory sequences.

6. An isolated transformed host cell comprising the isolated nucleic acid molecule of claim 1.

7. The transformed host cell of claim 5 wherein the host cell is selected from the group consisting of bacteria, yeast, filamentous fungi, algae, and green plants.

8. The transformed host cell of claim 7 wherein the host cell is selected from the group consisting of *Aspergillus, Trichoderma, Saccharomyces, Pichia, Candida, Hansenula, Phaffia, Yarrowia, Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus.*

9. A method for the production of astaxanthin comprising:
   (a) providing a host cell that produces a cyclic hydroxylated carotenoid intermediate selected from the group consisting of β-cryptoxanthin, 3-hydroxyechinenone, 3'-hydroxyechinenone, zeaxanthin, and adonixanthin;
   (b) transforming the host cell of (a) with the nucleic acid molecule of claim 1 operably linked to suitable regulatory sequences;
   (c) growing the transformed host cell of (b) under conditions whereby astaxanthin is produced.

10. The method according to claim 9 wherein the transformed host is selected from the group consisting of bacteria, yeast, filamentous fungi, algae, and green plants.

11. A method according to claim 10 wherein the transformed host cell is selected form the group consisting of *Aspergillus, Trichoderma, Saccharomyces, Pichia, Candida, Yarrowia, Phaffia, Hansenula, Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus.*

* * * * *

SEQUENCE LISTING

```
<160> NUMBER OF SEQ ID NOS: 23

<210> SEQ ID NO 1
<211> LENGTH: 729
<212> TYPE: DNA
<213> ORGANISM: Paracoccus sp. N81106
<220> FEATURE:
<221> NAME/KEY: CDS
<222> LOCATION: (1)..(729)

<400> SEQUENCE: 1
```

```
atg agc gca cat gcc ctg ccc aag gca gat ctg acc gcc acc agc ctg      48
Met Ser Ala His Ala Leu Pro Lys Ala Asp Leu Thr Ala Thr Ser Leu
1               5                   10                  15 atc gtc tcg ggc ggc atc atc gcc gct tgg ctg gcc ctg cat gtg cat      96
Ile Val Ser Gly Gly Ile Ile Ala Ala Trp Leu Ala Leu His Val His
            20                  25                  30 gcg ctg tgg ttt ctg gac gca gcg gcg cat ccc atc ctg gcg atc gca     144
Ala Leu Trp Phe Leu Asp Ala Ala Ala His Pro Ile Leu Ala Ile Ala
        35                  40                  45 aat ttc ctg ggg ctg acc tgg ctg tcg gtc gga ttg ttc atc atc gcg     192
Asn Phe Leu Gly Leu Thr Trp Leu Ser Val Gly Leu Phe Ile Ile Ala
    50                  55                  60 cat gac gcg atg cac ggg tcg gtg gtg ccg ggg cgt ccg cgc gcc aat     240
His Asp Ala Met His Gly Ser Val Val Pro Gly Arg Pro Arg Ala Asn
65                  70                  75                  80 gcg gcg atg ggc cag ctt gtc ctg tgg ctg tat gcc gga ttt tcg tgg     288
Ala Ala Met Gly Gln Leu Val Leu Trp Leu Tyr Ala Gly Phe Ser Trp
                85                  90                  95 cgc aag atg atc gtc aag cac atg gcc cat cac cgc cat gcc gga acc     336
Arg Lys Met Ile Val Lys His Met Ala His His Arg His Ala Gly Thr
            100                 105                 110 gac gac gac ccc gat ttc gac cat ggc ggc ccg gtc cgc tgg tac gcc     384
Asp Asp Asp Pro Asp Phe Asp His Gly Gly Pro Val Arg Trp Tyr Ala
        115                 120                 125 cgc ttc atc ggc acc tat ttc ggc tgg cgc gag ggg ctg ctg ctg ccc     432
Arg Phe Ile Gly Thr Tyr Phe Gly Trp Arg Glu Gly Leu Leu Leu Pro
    130                 135                 140 gtc atc gtg acg gtc tat gcg ctg atc ctt ggg gat cgc tgg atg tac     480
Val Ile Val Thr Val Tyr Ala Leu Ile Leu Gly Asp Arg Trp Met Tyr
145                 150                 155                 160 gtg gtc ttc tgg ccg ctg ccg tcg atc ctg gcg tcg atc cag ctg ttc     528
Val Val Phe Trp Pro Leu Pro Ser Ile Leu Ala Ser Ile Gln Leu Phe
                165                 170                 175 gtg ttc ggc acc tgg ctg ccg cac cgc ccc ggc cac gac gcg ttc ccg     576
Val Phe Gly Thr Trp Leu Pro His Arg Pro Gly His Asp Ala Phe Pro
            180                 185                 190 gac cgc cac aat gcg cgg tcg tcg cgg atc agc gac ccc gtg tcg ctg     624
Asp Arg His Asn Ala Arg Ser Ser Arg Ile Ser Asp Pro Val Ser Leu
        195                 200                 205 ctg acc tgc ttt cac ttt ggc ggt tat cat cac gaa cac cac ctg cac     672
Leu Thr Cys Phe His Phe Gly Gly Tyr His His Glu His His Leu His
    210                 215                 220 ccg acg gtg ccg tgg tgg cgc ctg ccc agc acc cgc acc aag ggg gac     720
Pro Thr Val Pro Trp Trp Arg Leu Pro Ser Thr Arg Thr Lys Gly Asp
225                 230                 235                 240 acc gca tga                                                          729
Thr Ala
```

<210> SEQ ID NO 2
<211> LENGTH: 242
<212> TYPE: PRT
<213> ORGANISM: Paracoccus sp. N81106

<400> SEQUENCE: 2

```
Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala Ala His Pro Ile Leu Ala Ile Ala
        35                  40                  45
```

-continued

```
Asn Phe Leu Gly Leu Thr Trp Leu Ser Val Gly Leu Phe Ile Ile Ala
 50                  55                  60

His Asp Ala Met His Gly Ser Val Val Pro Gly Arg Pro Arg Ala Asn
 65                  70                  75                  80

Ala Ala Met Gly Gln Leu Val Leu Trp Leu Tyr Ala Gly Phe Ser Trp
                 85                  90                  95

Arg Lys Met Ile Val Lys His Met Ala His Arg His Ala Gly Thr
            100                 105                 110

Asp Asp Asp Pro Asp Phe Asp His Gly Gly Pro Val Arg Trp Tyr Ala
            115                 120                 125

Arg Phe Ile Gly Thr Tyr Phe Gly Trp Arg Glu Gly Leu Leu Leu Pro
            130                 135                 140

Val Ile Val Thr Val Tyr Ala Leu Ile Leu Gly Asp Arg Trp Met Tyr
145                 150                 155                 160

Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
            180                 185                 190

Asp Arg His Asn Ala Arg Ser Ser Arg Ile Ser Asp Pro Val Ser Leu
            195                 200                 205

Leu Thr Cys Phe His Phe Gly Tyr His His Glu His His Leu His
            210                 215                 220

Pro Thr Val Pro Trp Trp Arg Leu Pro Ser Thr Arg Thr Lys Gly Asp
225                 230                 235                 240

Thr Ala

<210> SEQ ID NO 3
<211> LENGTH: 23
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (15)..(19)
<223> OTHER INFORMATION: alpha-thiol linkages

<400> SEQUENCE: 3
tgttacaacc aattaaccaa ttc                                        23

<210> SEQ ID NO 4
<211> LENGTH: 38
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (15)..(19)
<223> OTHER INFORMATION: alpha-thiol linkages

<400> SEQUENCE: 4
cgcgctagaa ttccaccatc atacactaaa tcagtaag                        38

<210> SEQ ID NO 5
<211> LENGTH: 489
<212> TYPE: DNA
<213> ORGANISM: Paracoccus sp. N81106
<220> FEATURE:
<221> NAME/KEY: CDS
<222> LOCATION: (1)..(489)
```

<400> SEQUENCE: 5

```
atg acc aat ttc ctg atc gtc gtc gcc acc gtg ctg gtg atg gag ttg      48
Met Thr Asn Phe Leu Ile Val Val Ala Thr Val Leu Val Met Glu Leu
1               5                   10                  15 acg gcc tat tcc gtc cac cgc tgg atc atg cac ggc ccc ctg ggc tgg      96
Thr Ala Tyr Ser Val His Arg Trp Ile Met His Gly Pro Leu Gly Trp
            20                  25                  30 ggc tgg cac aag tcc cac cac gag gaa cac gac cac gcg ctg gaa aag     144
Gly Trp His Lys Ser His His Glu Glu His Asp His Ala Leu Glu Lys
        35                  40                  45 aac gac ctg tac ggc ctg gtc ttt gcg gtg atc gcc acg gtg ctg ttc     192
Asn Asp Leu Tyr Gly Leu Val Phe Ala Val Ile Ala Thr Val Leu Phe
    50                  55                  60 acg gtg ggc tgg atc tgg gcg ccg gtc ctg tgg tgg atc gcc ttg ggc     240
Thr Val Gly Trp Ile Trp Ala Pro Val Leu Trp Trp Ile Ala Leu Gly
65                  70                  75                  80 atg act gtc tat ggg ctg atc tat ttc gtc ctg cat gac ggg ctg gtg     288
Met Thr Val Tyr Gly Leu Ile Tyr Phe Val Leu His Asp Gly Leu Val
                85                  90                  95 cat cag cgc tgg ccg ttc cgt tat atc ccg cgc aag ggc tat gcc aga     336
His Gln Arg Trp Pro Phe Arg Tyr Ile Pro Arg Lys Gly Tyr Ala Arg
            100                 105                 110 cgc ctg tat cag gcc cac cgc ctg cac cat gcg gtc gag ggg cgc gac     384
Arg Leu Tyr Gln Ala His Arg Leu His His Ala Val Glu Gly Arg Asp
        115                 120                 125 cat tgc gtc agc ttc ggc ttc atc tat gcg ccc ccg gtc gac aag ctg     432
His Cys Val Ser Phe Gly Phe Ile Tyr Ala Pro Pro Val Asp Lys Leu
    130                 135                 140 aag cag gac ctg aag atg tcg ggc gtg ctg cgg gcc gag gcg cag gag     480
Lys Gln Asp Leu Lys Met Ser Gly Val Leu Arg Ala Glu Ala Gln Glu
145                 150                 155                 160 cgc acg tga                                                         489
Arg Thr
```

<210> SEQ ID NO 6
<211> LENGTH: 162
<212> TYPE: PRT
<213> ORGANISM: Paracoccus sp. N81106

<400> SEQUENCE: 6

```
Met Thr Asn Phe Leu Ile Val Val Ala Thr Val Leu Val Met Glu Leu
1               5                   10                  15

Thr Ala Tyr Ser Val His Arg Trp Ile Met His Gly Pro Leu Gly Trp
            20                  25                  30

Gly Trp His Lys Ser His His Glu Glu His Asp His Ala Leu Glu Lys
        35                  40                  45

Asn Asp Leu Tyr Gly Leu Val Phe Ala Val Ile Ala Thr Val Leu Phe
    50                  55                  60

Thr Val Gly Trp Ile Trp Ala Pro Val Leu Trp Trp Ile Ala Leu Gly
65                  70                  75                  80

Met Thr Val Tyr Gly Leu Ile Tyr Phe Val Leu His Asp Gly Leu Val
                85                  90                  95

His Gln Arg Trp Pro Phe Arg Tyr Ile Pro Arg Lys Gly Tyr Ala Arg
            100                 105                 110

Arg Leu Tyr Gln Ala His Arg Leu His His Ala Val Glu Gly Arg Asp
        115                 120                 125

His Cys Val Ser Phe Gly Phe Ile Tyr Ala Pro Pro Val Asp Lys Leu
```

130                 135                 140
Lys Gln Asp Leu Lys Met Ser Gly Val Leu Arg Ala Glu Ala Gln Glu
145                 150                 155                 160

Arg Thr

<210> SEQ ID NO 7
<211> LENGTH: 54
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (15)..(19)
<223> OTHER INFORMATION: alpha-thiol linkages

<400> SEQUENCE: 7
aattggttgt aacagaattc cctaggtcta gaaaggagga ataaaccatg acca       54

<210> SEQ ID NO 8
<211> LENGTH: 45
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (15)..(19)
<223> OTHER INFORMATION: alpha-thiol linkages

<400> SEQUENCE: 8
ctcgactaga attgtgtaca ttaggtgcgt tcttgggctt cggca                 45

<210> SEQ ID NO 9
<211> LENGTH: 6384
<212> TYPE: DNA
<213> ORGANISM: artificial sequence
<220> FEATURE:
<223> OTHER INFORMATION: crt333 gene cluster comprising crtWEidiYIB
      coding regions

<400> SEQUENCE: 9
aattcactag aattgaagga ggaataaacc atgagcgccc atgccctgcc gaaagccgac   60
ctgaccgcga ccagcctgat cgtcagcggt ggcatcatcg cggcctggct ggcgctgcat  120
gtccatgccc tgtggttcct ggacgccgcc gcccatccga tcctggccat cgccaacttc  180
ctgggcctga cctggctgag cgtcggcctg ttcatcatcg cgcatgacgc catgcatggc  240
agcgtggtcc cgggtcgtcc gcgtgccaac gccgccatgg ccaactggt cctgtggttg   300 tatgccggct tcagctggcg caagatgatc gtcaaacata tggcccatca tcgccacgcg  360
ggcaccgacg acgatccgga cttcgaccat ggtggcccgg tccgctggta tgcgcgcttc  420
atcggcacct atttcggctg gcgtgaaggc tgttgctgc cggtcatcgt caccgtctat  480
gcgctgatcc tgggcgaccg ctggatgtat gtcgtcttct ggccgctgcc gagcatcctg  540
gcgagcatcc aactgttcgt cttcggtacc tggctgccgc atcgcccggg ccatgacgcc  600
tttccggacc gccataacgc ccgcagcagc cgcatcagcg acccggtcag cctgctgacc  660
tgcttccatt tcggcggcta tcatcatgaa catcatctgc atccgaccgt cccgtggtgg  720
cgcctgccga gcacccgcac caaaggcgac accgcgtgac aattctagtc gagacgccgg  780
gtaccaacca tgcacaagac cttttgaaaca catcccggtc acgacgggga actgcatgag  840
ctgcacgctg ccctgcaacg tcgcctggat gaactgctgc ccgttggcga tgagcgggat  900

-continued

```
cgggtcagca gcgcaatgcg cgaaggcgta ctggcaccgg ggaaacgcat tcgcccgctg      960
ctcctgatcc tcgccgcccg cgacctcggc tgcgatcgcg accaccccgg cctgctggat     1020
atggcctgtg cggtggaaat ggtgcacgcc tcgtcgctga tcctcgacga tattccctgc     1080
atggataacg cggcgctccg gcgcggtcgc cctaccattc atcgccagta tggtgaagac     1140
gtggcaattc tcgctgcggt agcgttgctc agcagcgcct ttggcgtgat ggtcgcggcg     1200
cagggattgt ctcccgagtg ccgcagccag gcggtggcgg agctgtcgat ggcggtcggt     1260
acccagggtc tggtgcaggg tcagtataag gatctgcgtg aaggcaccgc cccgcgcagc     1320
gccgaggaga tcgccaccac caacgaactg aaaaccagcg tgctgtttgg tgccacgctg     1380
caaatcgcgg ccctggcggc aggcgcctcg ccggcggcgc gccagaaaat gcgctgcttt     1440
gcgcaggatt taggccaggc gttccagctg ctggacgatc tggcggacgg ccatgccggg     1500
accggcaaag acatcaataa ggacgcgggt aagtccacgc tggtggcgat gctcggcagc     1560
gacgcggtgc gcgagcggct cgacacccat ctgcgccgcg cagacgccca tttttcacgc     1620
gcctgcggaa aaaaccaggc cacgcgacgc tttatgcacg cctggttttc aaaacagctg     1680
gccgcgttta gctgagcaac ggatacaccc cggtaatatt tgtggagatc acatgaagga     1740
cgcgcatctg gttcagcgta aaaatgacca cctggatatc gtgctgcacc ctgaccgggc     1800
gatgagtacc attcgcaccg gatttgacgc ctggcgtttt gaacactgcg ccctcccgga     1860
gctggatctc gacggtatcg atctctccac caccctgttt tcccgcccgc tgaaagcccc     1920
ggtgctgatc agctccatga ccggcggcgc ggcgcgcgcc agagacatta ccgtcatct     1980
ggcccaggcg gcgcaaaccc ttgggctggc gatgggcgtc ggttcccagc gcgtggcgct     2040
ggaggacggc gcgcagcacg ggctggatgc ccagctacgc catatcgccc cggacgtgcc     2100
gctgctggct aaccttggcg cggcgcagat ccgcggtgcg caggggctgg actacgcccg     2160
gcgcgcggtg gacatgatcg acgccgacgc gttaattgtg catctgaacc cgctgcagga     2220
ggcgctccag ggcggcggcg atcgcgactg gcgcggcatc ctcaacgcca ttgcgcagct     2280
ggtgcgcgac ctgccggtac cggtggtggt taaagaggtg ggcgccggga tctcccggga     2340
cgttgcctgc cgactggcgg acgtcggcgt ggcgatgatc gacattgccg gcgcgggcgg     2400
aaccagctgg gcgcggtgg aagctgaacg cgccccgacc cccgaggcgc gaaatgtggc     2460
gatggccttt gccgactggg gcattcctac tgccgatgcg ctgcgtcgcg tccatcttgc     2520
gctgcctgat atcccgctta tcgcctccgg cggcatcgcc aacggcattg acgcagcaaa     2580
agccatcgcg ctgggtgcag atctggtggg ccaggccgcg gcggtgctgg cgcatgccaa     2640
cgcctccggc gacgcggcaa ttgcccattt ccgcacctg attacgcagc tgcggatcgc     2700
ctgtttctgt accggcagtg caaacctgca ggcgttgcga cacgccacgc tgcttccggt     2760
caacggcggc gcatccctgt gacgcagtac ggtgccttat accggggagc ggtatgaaaa     2820
aatgggatct gattctggtc ggcgcggggc tggccaacgg gcttatcgcc tggcgactaa     2880
agcagcgtca tccgacgctt gctgtattaa tgctggagtg cggcgacgcg cccggcggaa     2940
accacacctg gtcctttcac caacacgata tcacgccagc cagcacgcc tggctggcgc     3000
cgctggtggc ccatcgctgg gacgggtacg acgtccactt tccgaacgtg tcgcgcaccc     3060
tgcatgacgg ctacctgacc atcacctcca cgcgttttgc ccaagcgatg cgcgggctga     3120
tgaaagagaa tttgctgaca aacgtgaccg tgtcacgggt gagcgggcag gaagtaaccc     3180
tcagcgacgg acgacgcttt accgccgggg cggtgattga tggccgcggc tatcagccct     3240
```

```
cgccgcacct cagcattggc tatcaggcgt tcatcggcca ggagtggcaa ctgaccgcgc   3300
cccacgggtt aacgcgcccg atcctgatgg atgcccgcgt cgcccagggc aacggctacc   3360
gctttgtcta tacccctgccg ctcagcgccg acaccctgct tatcgaagac acgcactaca   3420
ttgacggccc gacgctcgac gccgattcag cccgcgcgcg gattgccgat tacgcccgcc   3480
agcagggctg gcagcttgcg cggctggtgc gtgaggaaca gggggcgctg ccgatcaccc   3540
tgtccggcga tccggccgcc ttctggcacc agttccatca tcagccggtc agcggcctgc   3600
gcgccggtct gttccatgcc accaccggct attcgctgcc gctggcggtt cggctggcgg   3660
accgcattgc caacgcgccg ggactgcatc agggcgcgct ctatcagctg atcgccgatt   3720 cgcggcgcg ccactggcag acacaacgct ttttccgcct gcttaaccgc atgcttttcc   3780
tggccggcac acccgaccag cgctggcgcg tgatgcagcg gttttaccag cttgacgagc   3840
agctgatcgc ccgttttat gccggccagc ttcgctccgc cgaccgcgcg cgcctgctgc   3900
ttggcaaacc gccggtgccg attgtcgggg cgatcaaagc cctgctccac actcattctt   3960
ctctgcgagc ccatcataaa tgaaacaaac cattgtaatt ggcgccgggt tcggcggact   4020
ggcgctggcg attcgcctcc aggcggcggg cattcctacc acgctgctgg agagccgcga   4080
caaacccggc ggccgcgcct atgtctacga agatcgcggc tttacctttg atgcgggtcc   4140
caccgtcatc accgatccct ccgccattga ggagctgttc accctcgccg aaaacggct   4200 gaaggactac gttgagctga tgccggtgac gccgttctat cgcctgtgct gggaagacgg   4260
caaggttttc gactacgcca acgatcaggc ggcgcttgag tcgcagatcg ccgcgtttaa   4320
cccgaacgac gtggcgggct atcaccgctt cctcgactac tcccgggcgg tgtttgccga   4380
aggctatctg aagctcggcg cggtgccgtt tctctcgttt cgcgacatgc tgcgcgccgg   4440
tcctcaactg gcgcggctgc aggcatggcg cagcgtgtac gacaaagtgt cggcctacgt   4500
ggaagacgag cacctgcggc aggcattttc gtttcactcg ctgctggtgg gcggcaaccc   4560
gttctccacg tcttctattt acaccctgat ccacgccctg gagcgggaat ggggcgtctg   4620
gttcccgcgc ggcggcaccg gtgcgctggt caggcatg gtgaagctgt tcaggatct   4680 tggcggcacc ctcaccctta acgctcaggt tgagcggctg gagacggtgg acaatcaggt   4740
gaaggccgtg catctggtta acgggcagcg gctggaggct gcggcggtgg cctcgaacgc   4800
ggacgtggta aatacctatg cccgactgct cggccatcac ccgcacggcg ccgctacggc   4860
caaaaagctg aaacgcaagc gcatgagcaa ctcgctgttc gtgctctatt ttggcctgga   4920
tcaccatcac acccagctgg cgcaccatac cgtctgcttt ggcccgcgtt ataaagcgct   4980
aatcgatgaa attttcagcg ccgacaccct gtcggaagat ttttcgctct atctgcatgc   5040
gccctgcgta accgacccgt cgctggcccc gccggggtgc ggcagctact atgtgctcgc   5100
gccggtgccg cacctcggta acgcccgct cgactggagc gtggaagggc gcgtctgcg   5160 ggatcgcatt tttgattatc tcgaagcgcg ctatatgccg gggctgcgct cccagctggt   5220
gacgcaccgc atgttcacgc cggaagattt tcgcgatacg ctcgatgcct ggcaggggtc   5280
agcgttttca ctggagccga tcctcaccca gagcgcctgg ttccggccgc acaaccgcga   5340
cagcgtggtt gataacctct acctggtcgg cgccggaacg catcccggcg ctggcgtgcc   5400
gggcgtgatc ggatccgcca aggcaacggc ccagttaatg ttaaaggatt tagcgtaatg   5460
tcccagccgc ttctcgaaca cgccagcgcc accatgaccg ccggttctaa aagtttcgcc   5520
accgcctcaa agctgtttga caaacgcacc cggcgcagcg cgctgatgct ctatacctgg   5580
tgccgctact gcgacgatgt tatcgacgga caggtggtgg gttttgctgc cccgaccgag   5640
```

```
cagagcgaca cgcccgaggc gcgcctgcaa cggctgcgta agatgacgcg ccgcgcctac    5700
gacggggaaa ccatgcaaga gccgccgttc gccgcctttc aggaggttgc cctcgcccat    5760
gccattccgc ctactcaggc cttcgaccac ctggaaggct atgcgatgga cgtgcgcaac    5820
gagcgctatt acagcctcga tgatacgctc cgctactgtt atcacgtggc gggcgtggtc    5880
ggcctgatga tggccagggt gatgggagtg cgggacgaag ccacgctgga tcgcgcctgc    5940
gatctgggca ttgcctttca gctcaccaat atcgccaggg atatcgttga cgatgcgcag    6000
gtgggacgct gctacctgcc gcagcagtgg ctggcggaag tcggactcaa tgaacagacc    6060
tgcaccgtgc gggccaaccg tccggcgctg gcgcgtctgg cagcgcggct ggtgaccgag    6120
gctgagccct attatcagtc agcgcttgcc gggctggggg atctgcccct cgctccgcc     6180 tgggcgattg ccaccgcgca cggggtgtat cgtgagatcg gggtgaaggt gctgatggcg    6240
ggtgaaaaag catgggatac ccgccagggc acgacgcgcg cggagaagct ggcgctggtt    6300
atttccggcg cgaagcaggc gatggcttcc cggaaggcga gctggccgcc gcgcgatccg    6360
cacctctggc agcgcccgcg ctag                                           6384
```

<210> SEQ ID NO 10
<211> LENGTH: 56
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (15)..(19)
<223> OTHER INFORMATION: alpha-thiol linkages

<400> SEQUENCE: 10
caattctagt cgagacgccg ggtaccaacc atgacaagac cctttgaaac acatcc        56

<210> SEQ ID NO 11
<211> LENGTH: 37
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (15)..(19)
<223> OTHER INFORMATION: alpha-thiol linkages

<400> SEQUENCE: 11
atcagatccc attttttcat accgctcccc ggtataa                             37

<210> SEQ ID NO 12
<211> LENGTH: 25
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (15)..(19)
<223> OTHER INFORMATION: alpha-thiol linkages

<400> SEQUENCE: 12
aaatgggatc tgattctggt cggcg                                          25

<210> SEQ ID NO 13
<211> LENGTH: 25
<212> TYPE: DNA

<213> ORGANISM: artificial sequence
<220> FEATURE:
<223> OTHER INFORMATION: primer
<220> FEATURE:
<221> NAME/KEY: misc_feature
<222> LOCATION: (15)..(19)
<223> OTHER INFORMATION: alpha-thiol linkages

<400> SEQUENCE: 13
ggaattctag cgcgggcgct gccag                                          25

<210> SEQ ID NO 14
<211> LENGTH: 48
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (25)..(29)
<223> OTHER INFORMATION: alpha-thiol linkages

<400> SEQUENCE: 14
taacgatgca aaacgcatcc tgccaccatc atacactaaa tcagtaag                 48

<210> SEQ ID NO 15
<211> LENGTH: 48
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (25)..(29)
<223> OTHER INFORMATION: alpha-thiol linkages

<400> SEQUENCE: 15
tttcagcgac aactcctgca ttggcatacg agccggaagc ataaagtg                 48

<210> SEQ ID NO 16
<211> LENGTH: 26
<212> TYPE: DNA
<213> ORGANISM: artificial sequence
<220> FEATURE:
<223> OTHER INFORMATION: primer

<400> SEQUENCE: 16
tcatccggaa ttcactagta aggagg                                         26

<210> SEQ ID NO 17
<211> LENGTH: 39
<212> TYPE: DNA
<213> ORGANISM: artificial sequence
<220> FEATURE:
<223> OTHER INFORMATION: primer

<400> SEQUENCE: 17
atcaattgga gctcgtttat tcctcctttc tagatcacg                           39

<210> SEQ ID NO 18
<211> LENGTH: 729
<212> TYPE: DNA
<213> ORGANISM: artificial sequence
<220> FEATURE:
<223> OTHER INFORMATION: Mutant ketolase L175M
<220> FEATURE:
<221> NAME/KEY: CDS
<222> LOCATION: (1)..(729)

```
<400> SEQUENCE: 18 atg agc gcc cat gcc ctg ccg aaa gcc gac ctg acc gcg acc agc ctg      48
Met Ser Ala His Ala Leu Pro Lys Ala Asp Leu Thr Ala Thr Ser Leu
1               5                   10                  15 atc gtc agc ggt ggc atc atc gcg gcc tgg ctg gcg ctg cat gtc cat      96
Ile Val Ser Gly Gly Ile Ile Ala Ala Trp Leu Ala Leu His Val His
            20                  25                  30 gcc ctg tgg ttc ctg gac gcc gcc gcc cat ccg atc ctg gcc atc gcc     144
Ala Leu Trp Phe Leu Asp Ala Ala Ala His Pro Ile Leu Ala Ile Ala
        35                  40                  45 aac ttc ctg ggc ctg acc tgg ctg agc gtc ggc ctg ttc atc atc gcg     192
Asn Phe Leu Gly Leu Thr Trp Leu Ser Val Gly Leu Phe Ile Ile Ala
    50                  55                  60 cat gac gcc atg cat ggc agc gtg gtc ccg ggt cgt ccg cgt gcc aac     240
His Asp Ala Met His Gly Ser Val Val Pro Gly Arg Pro Arg Ala Asn
65                  70                  75                  80 gcc gcc atg ggc caa ctg gtc ctg tgg ttg tat gcc ggc ttc agc tgg     288
Ala Ala Met Gly Gln Leu Val Leu Trp Leu Tyr Ala Gly Phe Ser Trp
                85                  90                  95 cgc aag atg atc gtc aaa cat atg gcc cat cat cgc cac gcg ggc acc     336
Arg Lys Met Ile Val Lys His Met Ala His His Arg His Ala Gly Thr
            100                 105                 110 gac gac gat ccg gac ttc gac cat ggt ggc ccg gtc cgc tgg tat gcg     384
Asp Asp Asp Pro Asp Phe Asp His Gly Gly Pro Val Arg Trp Tyr Ala
        115                 120                 125 cgc ttc atc ggc acc tat ttc ggc tgg cgt gaa ggc ctg ttg ctg ccg     432
Arg Phe Ile Gly Thr Tyr Phe Gly Trp Arg Glu Gly Leu Leu Leu Pro
    130                 135                 140 gtc atc gtc acc gtc tat gcg ctg atc ctg ggc gac cgc tgg atg tat     480
Val Ile Val Thr Val Tyr Ala Leu Ile Leu Gly Asp Arg Trp Met Tyr
145                 150                 155                 160 gtc gtc ttc tgg ccg ctg ccg agc atc ctg gcg agc atc caa atg ttc     528
Val Val Phe Trp Pro Leu Pro Ser Ile Leu Ala Ser Ile Gln Met Phe
                165                 170                 175 gtc ttc ggt acc tgg ctg ccg cat cgc ccg ggc cat gac gcc ttt ccg     576
Val Phe Gly Thr Trp Leu Pro His Arg Pro Gly His Asp Ala Phe Pro
            180                 185                 190 gac cgc cat aac gcc cgc agc agc cgc atc agc gac ccg gtc agc ctg     624
Asp Arg His Asn Ala Arg Ser Ser Arg Ile Ser Asp Pro Val Ser Leu
        195                 200                 205 ctg acc tgc ttc cat ttc ggc ggc tat cat cat gaa cat cat ctg cat     672
Leu Thr Cys Phe His Phe Gly Gly Tyr His His Glu His His Leu His
    210                 215                 220 ccg acc gtc ccg tgg tgg cgc ctg ccg agc acc cgc acc aaa ggc gac     720
Pro Thr Val Pro Trp Trp Arg Leu Pro Ser Thr Arg Thr Lys Gly Asp
225                 230                 235                 240 acc gcg tga                                                         729
Thr Ala

<210> SEQ ID NO 19
<211> LENGTH: 242
<212> TYPE: PRT
<213> ORGANISM: artificial sequence
<220> FEATURE:
<223> OTHER INFORMATION: Synthetic Construct

<400> SEQUENCE: 19

Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
```

-continued

```
                    20                  25                  30
Ala Leu Trp Phe Leu Asp Ala Ala His Pro Ile Leu Ala Ile Ala
        35                  40                  45

Asn Phe Leu Gly Leu Thr Trp Leu Ser Val Gly Leu Phe Ile Ile Ala
 50                  55                  60

His Asp Ala Met His Gly Ser Val Val Pro Gly Arg Pro Arg Ala Asn
 65                  70                  75                  80

Ala Ala Met Gly Gln Leu Val Leu Trp Leu Tyr Ala Gly Phe Ser Trp
                 85                  90                  95

Arg Lys Met Ile Val Lys His Met Ala His His Arg His Ala Gly Thr
                100                 105                 110

Asp Asp Asp Pro Asp Phe Asp His Gly Gly Pro Val Arg Trp Tyr Ala
            115                 120                 125

Arg Phe Ile Gly Thr Tyr Phe Gly Trp Arg Glu Gly Leu Leu Leu Pro
130                 135                 140

Val Ile Val Thr Val Tyr Ala Leu Ile Leu Gly Asp Arg Trp Met Tyr
145                 150                 155                 160

Val Val Phe Trp Pro Leu Pro Ser Ile Leu Ala Ser Ile Gln Met Phe
                165                 170                 175

Val Phe Gly Thr Trp Leu Pro His Arg Pro Gly His Asp Ala Phe Pro
            180                 185                 190

Asp Arg His Asn Ala Arg Ser Ser Arg Ile Ser Asp Pro Val Ser Leu
            195                 200                 205

Leu Thr Cys Phe His Phe Gly Gly Tyr His His Glu His His Leu His
        210                 215                 220

Pro Thr Val Pro Trp Trp Arg Leu Pro Ser Thr Arg Thr Lys Gly Asp
225                 230                 235                 240

Thr Ala
```

```
<210> SEQ ID NO 20
<211> LENGTH: 729
<212> TYPE: DNA
<213> ORGANISM: artificial sequence
<220> FEATURE:
<223> OTHER INFORMATION: Mutant ketolase M99I
<220> FEATURE:
<221> NAME/KEY: CDS
<222> LOCATION: (1)..(729)

<400> SEQUENCE: 20
```

```
atg agc gcc cat gcc ctg ccg aaa gcc gac ctg acc gcg acc agc ctg      48
Met Ser Ala His Ala Leu Pro Lys Ala Asp Leu Thr Ala Thr Ser Leu
 1               5                  10                  15 atc gtc agc ggt ggc atc atc gcg gcc tgg ctg gcg ctg cat gtc cat      96
Ile Val Ser Gly Gly Ile Ile Ala Ala Trp Leu Ala Leu His Val His
                 20                  25                  30 gcc ctg tgg ttc ctg gac gcc gcc gcc cat ccg atc ctg gcc atc gcc     144
Ala Leu Trp Phe Leu Asp Ala Ala Ala His Pro Ile Leu Ala Ile Ala
         35                  40                  45 aac ttc ctg ggc ctg acc tgg ctg agc gtc ggc ctg ttc atc atc gcg     192
Asn Phe Leu Gly Leu Thr Trp Leu Ser Val Gly Leu Phe Ile Ile Ala
 50                  55                  60 cat gac gcc atg cat ggc agc gtg gtc ccg ggt cgt ccg cgt gcc aac     240
His Asp Ala Met His Gly Ser Val Val Pro Gly Arg Pro Arg Ala Asn
 65                  70                  75                  80 gcc gcc atg ggc caa ctg gtc ctg tgg ttg tat gcc ggc ttc agc tgg     288
Ala Ala Met Gly Gln Leu Val Leu Trp Leu Tyr Ala Gly Phe Ser Trp
                 85                  90                  95
```

-continued

| | | |
|---|---|---|
| cgc aag att atc gtc aaa cat atg gcc cat cat cgc cac gcg ggc acc<br>Arg Lys Ile Ile Val Lys His Met Ala His His Arg His Ala Gly Thr<br>    100                 105                 110 | | 336 |
| gac gac gat ccg gac ttc gac cat ggt ggc ccg gtc cgc tgg tat gcg<br>Asp Asp Asp Pro Asp Phe Asp His Gly Gly Pro Val Arg Trp Tyr Ala<br>115                 120                 125 | | 384 |
| cgc ttc atc ggc acc tat ttc ggc tgg cgt gaa ggc ctg ttg ctg ccg<br>Arg Phe Ile Gly Thr Tyr Phe Gly Trp Arg Glu Gly Leu Leu Leu Pro<br>    130                 135                 140 | | 432 |
| gtc atc gtc acc gtc tat gcg ctg atc ctg ggc gac cgc tgg atg tat<br>Val Ile Val Thr Val Tyr Ala Leu Ile Leu Gly Asp Arg Trp Met Tyr<br>145                 150                 155                 160 | | 480 |
| gtc gtc ttc tgg ccg ctg ccg agc atc ctg gcg agc atc caa ctg ttc<br>Val Val Phe Trp Pro Leu Pro Ser Ile Leu Ala Ser Ile Gln Leu Phe<br>                165                 170                 175 | | 528 |
| gtc ttc ggt acc tgg ctg ccg cat cgc ccg ggc cat gac gcc ttt ccg<br>Val Phe Gly Thr Trp Leu Pro His Arg Pro Gly His Asp Ala Phe Pro<br>            180                 185                 190 | | 576 |
| gac cgc cat aac gcc cgc agc agc cgc atc agc gac ccg gtc agc ctg<br>Asp Arg His Asn Ala Arg Ser Ser Arg Ile Ser Asp Pro Val Ser Leu<br>        195                 200                 205 | | 624 |
| ctg acc tgc ttc cat ttc ggc ggc tat cat cat gaa cat cat ctg cat<br>Leu Thr Cys Phe His Phe Gly Gly Tyr His His Glu His His Leu His<br>    210                 215                 220 | | 672 |
| ccg acc gtc ccg tgg tgg cgc ctg ccg agc acc cgc acc aaa ggc gac<br>Pro Thr Val Pro Trp Trp Arg Leu Pro Ser Thr Arg Thr Lys Gly Asp<br>225                 230                 235                 240 | | 720 |
| acc gcg tga<br>Thr Ala | | 729 |

<210> SEQ ID NO 21
<211> LENGTH: 242
<212> TYPE: PRT
<213> ORGANISM: artificial sequence
<220> FEATURE:
<223> OTHER INFORMATION: Synthetic Construct

<400> SEQUENCE: 21

Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala His Pro Ile Leu Ala Ile Ala
        35                  40                  45

Asn Phe Leu Gly Leu Thr Trp Leu Ser Val Gly Leu Phe Ile Ile Ala
    50                  55                  60

His Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Ile Ile Val Lys His Met Ala His His Arg His Ala Gly Thr
            100                 105                 110

Asp Asp Asp Pro Asp Phe Asp His Gly Gly Pro Val Arg Trp Tyr Ala
        115                 120                 125

Arg Phe Ile Gly Thr Tyr Phe Gly Trp Arg Glu Gly Leu Leu Leu Pro
    130                 135                 140

Val Ile Val Thr Val Tyr Ala Leu Ile Leu Gly Asp Arg Trp Met Tyr
145                 150                 155                 160

```
Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
                180                 185                 190

Asp Arg His Asn Ala Arg Ser Ser Arg Ile Ser Asp Pro Val Ser Leu
            195                 200                 205

Leu Thr Cys Phe His Phe Gly Gly Tyr His His Glu His His Leu His
        210                 215                 220

Pro Thr Val Pro Trp Trp Arg Leu Pro Ser Thr Arg Thr Lys Gly Asp
225                 230                 235                 240

Thr Ala

<210> SEQ ID NO 22
<211> LENGTH: 729
<212> TYPE: DNA
<213> ORGANISM: artificial sequence
<220> FEATURE:
<223> OTHER INFORMATION: Mutant ketolase M99V
<220> FEATURE:
<221> NAME/KEY: CDS
<222> LOCATION: (1)..(729)

<400> SEQUENCE: 22 atg agc gcc cat gcc ctg ccg aaa gcc gac ctg acc gcg acc agc ctg      48
Met Ser Ala His Ala Leu Pro Lys Ala Asp Leu Thr Ala Thr Ser Leu
1               5                   10                  15 atc gtc agc ggt ggc atc atc gcg gcc tgg ctg gcg ctg cat gtc cat      96
Ile Val Ser Gly Gly Ile Ile Ala Ala Trp Leu Ala Leu His Val His
                20                  25                  30 gcc ctg tgg ttc ctg gac gcc gcc gcc cat ccg atc ctg gcc atc gcc     144
Ala Leu Trp Phe Leu Asp Ala Ala Ala His Pro Ile Leu Ala Ile Ala
            35                  40                  45 aac ttc ctg ggc ctg acc tgg ctg agc gtc ggc ctg ttc atc atc gcg     192
Asn Phe Leu Gly Leu Thr Trp Leu Ser Val Gly Leu Phe Ile Ile Ala
        50                  55                  60 cat gac gcc atg cat ggc agc gtg gtc ccg ggt cgt ccg cgt gcc aac     240
His Asp Ala Met His Gly Ser Val Val Pro Gly Arg Pro Arg Ala Asn
65                  70                  75                  80 gcc gcc atg ggc caa ctg gtc ctg tgg ttg tat gcc ggc ttc agc tgg     288
Ala Ala Met Gly Gln Leu Val Leu Trp Leu Tyr Ala Gly Phe Ser Trp
                85                  90                  95 cgc aag gtt atc gtc aaa cat atg gcc cat cat cgc cac gcg ggc acc     336
Arg Lys Val Ile Val Lys His Met Ala His His Arg His Ala Gly Thr
            100                 105                 110 gac gac gat ccg gac ttc gac cat ggt ggc ccg gtc cgc tgg tat gcg     384
Asp Asp Asp Pro Asp Phe Asp His Gly Gly Pro Val Arg Trp Tyr Ala
        115                 120                 125 cgc ttc atc ggc acc tat ttc ggc tgg cgt gaa ggc ctg ttg ctg ccg     432
Arg Phe Ile Gly Thr Tyr Phe Gly Trp Arg Glu Gly Leu Leu Leu Pro
    130                 135                 140 gtc atc gtc acc gtc tat gcg ctg atc ctg ggc gac cgc tgg atg tat     480
Val Ile Val Thr Val Tyr Ala Leu Ile Leu Gly Asp Arg Trp Met Tyr
145                 150                 155                 160 gtc gtc ttc tgg ccg ctg ccg agc atc ctg gcg agc atc caa ctg ttc     528
Val Val Phe Trp Pro Leu Pro Ser Ile Leu Ala Ser Ile Gln Leu Phe
                165                 170                 175 gtc ttc ggt acc tgg ctg ccg cat cgc ccg ggc cat gac gcc ttt ccg     576
Val Phe Gly Thr Trp Leu Pro His Arg Pro Gly His Asp Ala Phe Pro
            180                 185                 190
```

```
gac cgc cat aac gcc cgc agc agc cgc atc agc gac ccg gtc agc ctg      624
Asp Arg His Asn Ala Arg Ser Ser Arg Ile Ser Asp Pro Val Ser Leu
        195                 200                 205 ctg acc tgc ttc cat ttc ggc ggc tat cat cat gaa cat cat ctg cat      672
Leu Thr Cys Phe His Phe Gly Gly Tyr His His Glu His His Leu His
210                 215                 220 ccg acc gtc ccg tgg tgg cgc ctg ccg agc acc cgc acc aaa ggc gac      720
Pro Thr Val Pro Trp Trp Arg Leu Pro Ser Thr Arg Thr Lys Gly Asp
225                 230                 235                 240 acc gcg tga                                                          729
Thr Ala
```

<210> SEQ ID NO 23
<211> LENGTH: 242
<212> TYPE: PRT
<213> ORGANISM: artificial sequence
<220> FEATURE:
<223> OTHER INFORMATION: Synthetic Construct

<400> SEQUENCE: 23

```
Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala His Pro Ile Leu Ala Ile Ala
        35                  40                  45

Asn Phe Leu Gly Leu Thr Trp Leu Ser Val Gly Leu Phe Ile Ile Ala
 50                  55                  60

His Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Val Ile Val Lys His Met Ala His His Arg His Ala Gly Thr
            100                 105                 110

Asp Asp Asp Pro Asp Phe Asp His Gly Gly Pro Val Arg Trp Tyr Ala
        115                 120                 125

Arg Phe Ile Gly Thr Tyr Phe Gly Trp Arg Glu Gly Leu Leu Leu Pro
    130                 135                 140

Val Ile Val Thr Val Tyr Ala Leu Ile Leu Gly Asp Arg Trp Met Tyr
145                 150                 155                 160

Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
            180                 185                 190

Asp Arg His Asn Ala Arg Ser Ser Arg Ile Ser Asp Pro Val Ser Leu
        195                 200                 205

Leu Thr Cys Phe His Phe Gly Gly Tyr His His Glu His His Leu His
    210                 215                 220

Pro Thr Val Pro Trp Trp Arg Leu Pro Ser Thr Arg Thr Lys Gly Asp
225                 230                 235                 240

Thr Ala
```